(12) United States Patent
Lovegrove

(10) Patent No.: US 11,890,508 B2
(45) Date of Patent: Feb. 6, 2024

(54) DETERMINING READINESS FOR AN OPERATIONAL TASK

(71) Applicant: Morphix, Inc., Vancouver, WA (US)

(72) Inventor: Jonathan Lovegrove, Yacolt, WA (US)

(73) Assignee: MORPHIX, INC., Vancouver, WA (US)

( * ) Notice: Subject to any disclaimer, the term of this patent is extended or adjusted under 35 U.S.C. 154(b) by 75 days.

(21) Appl. No.: 17/390,676

(22) Filed: Jul. 30, 2021

(65) Prior Publication Data
US 2023/0033838 A1 Feb. 2, 2023

(51) Int. Cl.
*A63B 24/00* (2006.01)
*G06N 20/00* (2019.01)
*A63B 71/06* (2006.01)

(52) U.S. Cl.
CPC ...... *A63B 24/0062* (2013.01); *A63B 71/0622* (2013.01); *G06N 20/00* (2019.01); *A63B 2024/0068* (2013.01); *A63B 2220/62* (2013.01); *A63B 2220/70* (2013.01); *A63B 2220/836* (2013.01)

(58) Field of Classification Search
CPC ............ A63B 24/0062; A63B 71/0622; A63B 2024/0068; A63B 2220/62; A63B 2220/70; A63B 2220/836; G06N 20/00
See application file for complete search history.

(56) References Cited

U.S. PATENT DOCUMENTS

2020/0233397 A1* 7/2020 Bello ..................... G06N 20/20

* cited by examiner

*Primary Examiner* — Robert P Bullington
(74) *Attorney, Agent, or Firm* — Alleman Hall Creasman & Tuttle LLP

(57) ABSTRACT

Examples are disclosed that relate to methods, computing devices, and systems for determining a user's readiness for an operational task. One example provides a method comprising, during a training phase, receiving training input data including, for each user training session, a training data pair including, as input, a distance of travel, a mode of travel, and one or more environmental conditions, and as ground truth output, a time elapsed for performance of the training task. An artificial intelligence (AI) performance model is trained to model user performance of the training task based on the training data pairs. During a run-time phase, operational input data is received that is associated with an operational task performed by the user. The performance model is used to infer a predicted time elapsed for performance of the operational task.

23 Claims, 18 Drawing Sheets

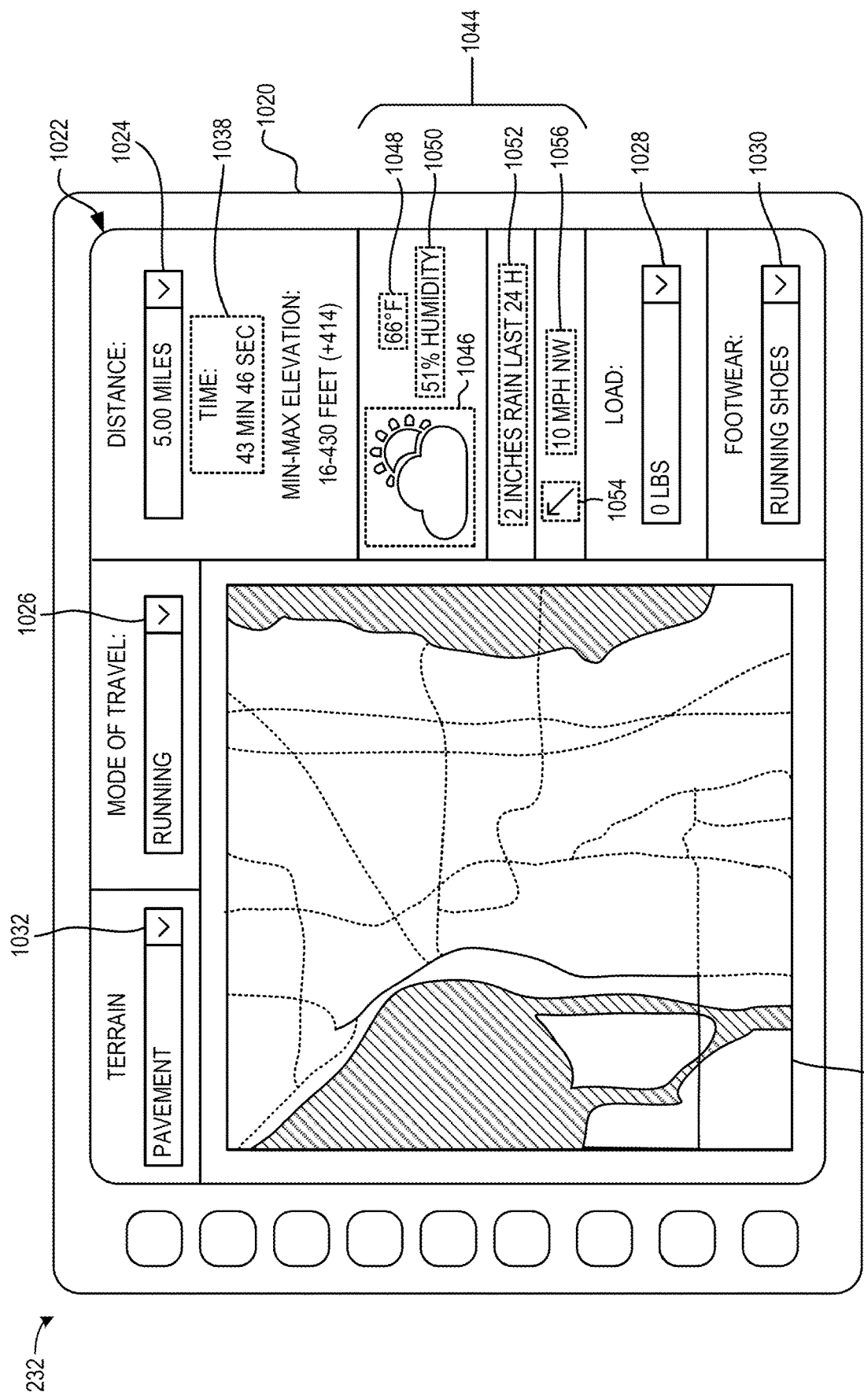

DETERMINING READINESS FOR AN OPERATIONAL TASK

BACKGROUND

Accurate knowledge of a person's performance and capabilities is a central aspect of military, emergency response, and commercial logistics operations. A leader or a dispatcher may instruct a person working alone or in a group with others in an operational environment to perform an operational task. However, it can be difficult to assess the person or the group's readiness for the operational task under various different conditions of the operational environment, given that the physical condition of the person and/or group may vary and be difficult to predict. As a result, a leader or dispatcher may instruct a person or group to perform an operational task that is beyond their abilities, or may refrain from doing so out of concern the task would be impossible to complete when in fact the person or group is well up to the task. In these situations, the person or group may fail to perform a requested operational task or suffer injury or harm in trying, or an operational task that could have been completed may remain unperformed.

SUMMARY

In view of the issues discussed above, according to one aspect of the present disclosure, a method is provided for determining a user's readiness for an operational task. The method comprises, at one or more processors of one or more computing devices: during a training phase, for each of a plurality of user training sessions associated with a training task performed by a user, receiving training input data. The training input data includes, for each user training session, a training data pair. The training data pair includes, as input, a distance of travel, a mode of travel, and one or more environmental conditions in which the training task is performed during the training session, and as ground truth output, a time elapsed for performance of the training task by the user during the training session. The one or more environmental conditions are selected from a plurality of predefined environmental conditions. During the training phase, an artificial intelligence (AI) performance model is trained that models user performance of the training task based on the training data pairs. The method further comprises, during a run-time phase: receiving operational input data associated with an operational task performed by the user. The operational input data includes a target distance of travel, a target mode of travel, and one or more target environmental conditions in which the operational task is performed. Based on the operational input data, the AI performance model is used to infer a predicted time elapsed for performance of the operational task. The method further comprises outputting the predicted time elapsed for performance of the operational task.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIGS. 6A-6B show graphical user interfaces of an example computing device that may be used in the field environment of FIG. 1C or remotely therefrom.

DETAILED DESCRIPTION

As introduced above, accurate knowledge of a person's performance and capabilities is a central aspect of military, emergency response, and commercial logistics operations. A leader or a dispatcher may instruct a person or a group working in an operational environment to perform an operational task. However, it can be difficult to assess an individual or a group's readiness for the operational task, given the different environmental conditions of the field environment, and varied physical condition of the persons or group members.

Figure 1A:
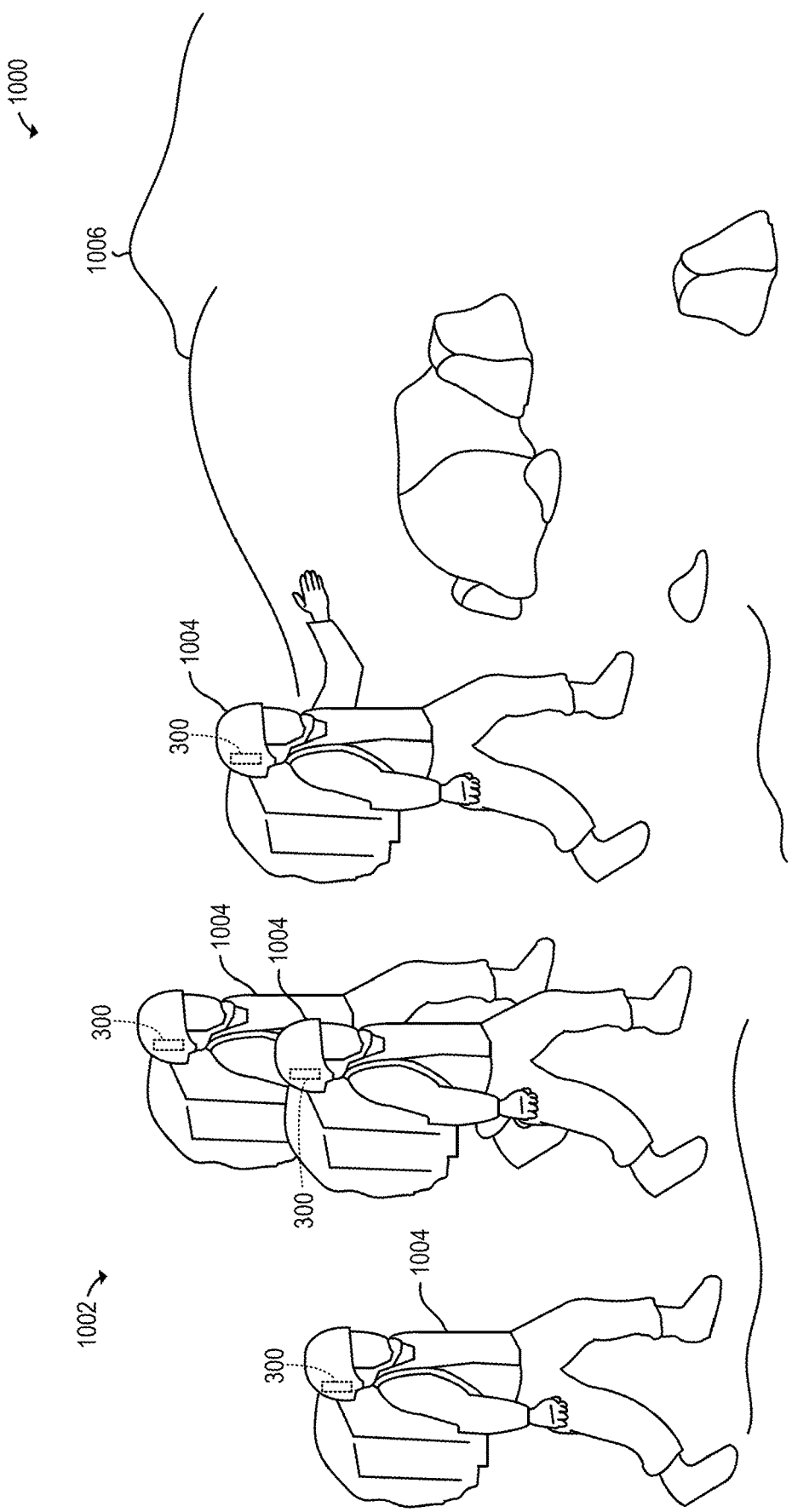
FIG. 1A shows one example of a field environment.
Figure 1B:
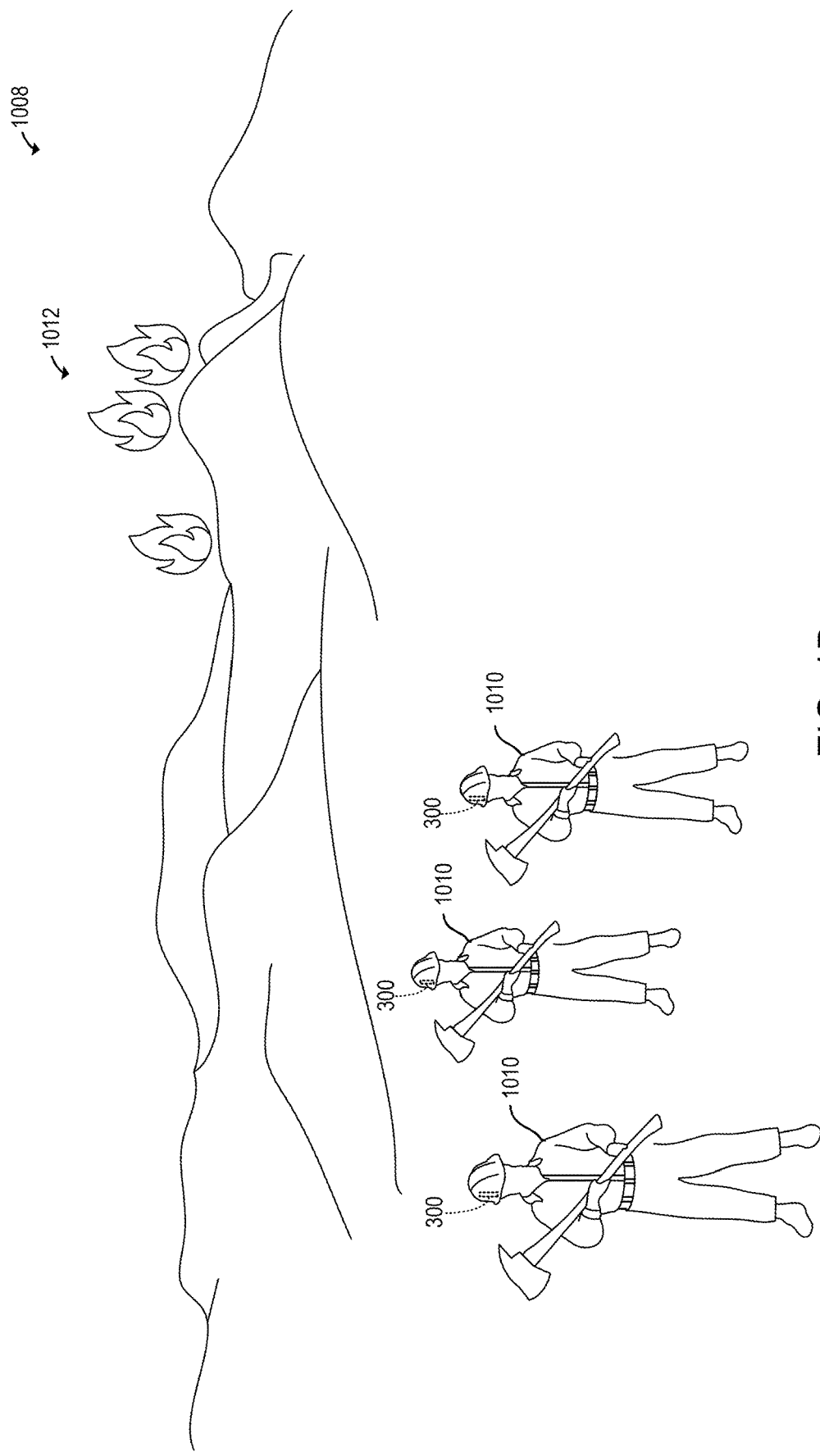
FIG. 1B shows another example of a field environment.
Figure 1C:
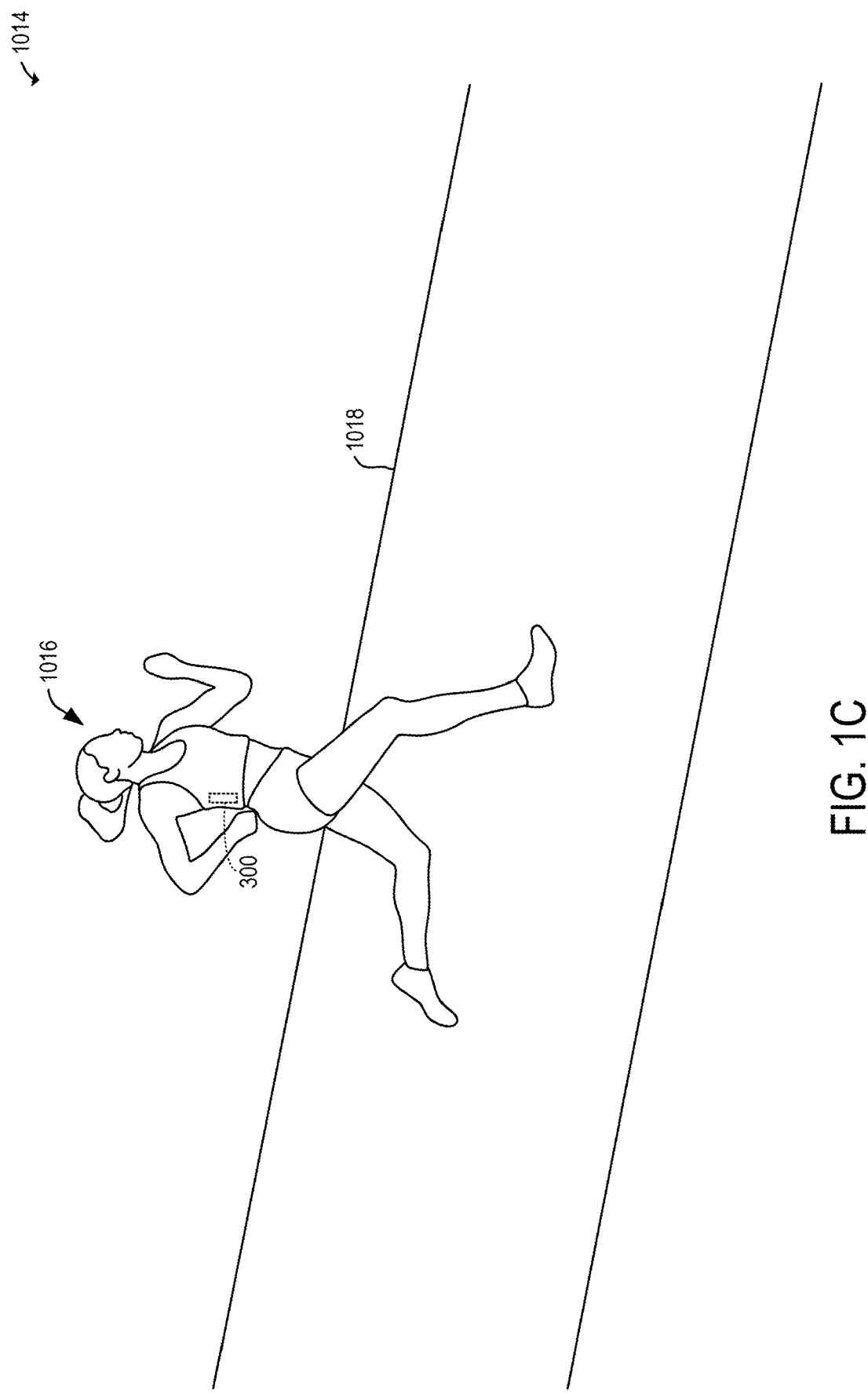
FIG. 1C shows another example of a field environment.

For example, FIG. 1A depicts one example of a field environment 1000 that can serve as an operational environment. A team 1002 of soldiers 1004 may be ordered to occupy an objective in the field, such as hilltop 1006 by a remote command post. FIG. 1B shows another example of a field environment 1008, in which a team of firefighters 1010 may be dispatched to a wildfire site 1012, and remotely commanded by a command center. FIG. 1C depicts another example of a field environment 1014, in which a user 1016 is completing a run on a paved pathway 1018, the user being coached by a coach or being self-coached. It will be appreciated that an amount of time it takes to achieve respective tasks such as these (e.g., marching, firefighting, or running) can vary based upon many different factors, including distance of travel, mode of travel, environmental conditions, pack weight/burden, terrain, physical training, and the physical condition of the persons or group such as level of fitness and level of rest or exhaustion. Accordingly, it can be challenging to determine whether an individual or a group can accomplish the operational task within a desired timeframe given the conditions.

Figure 2:
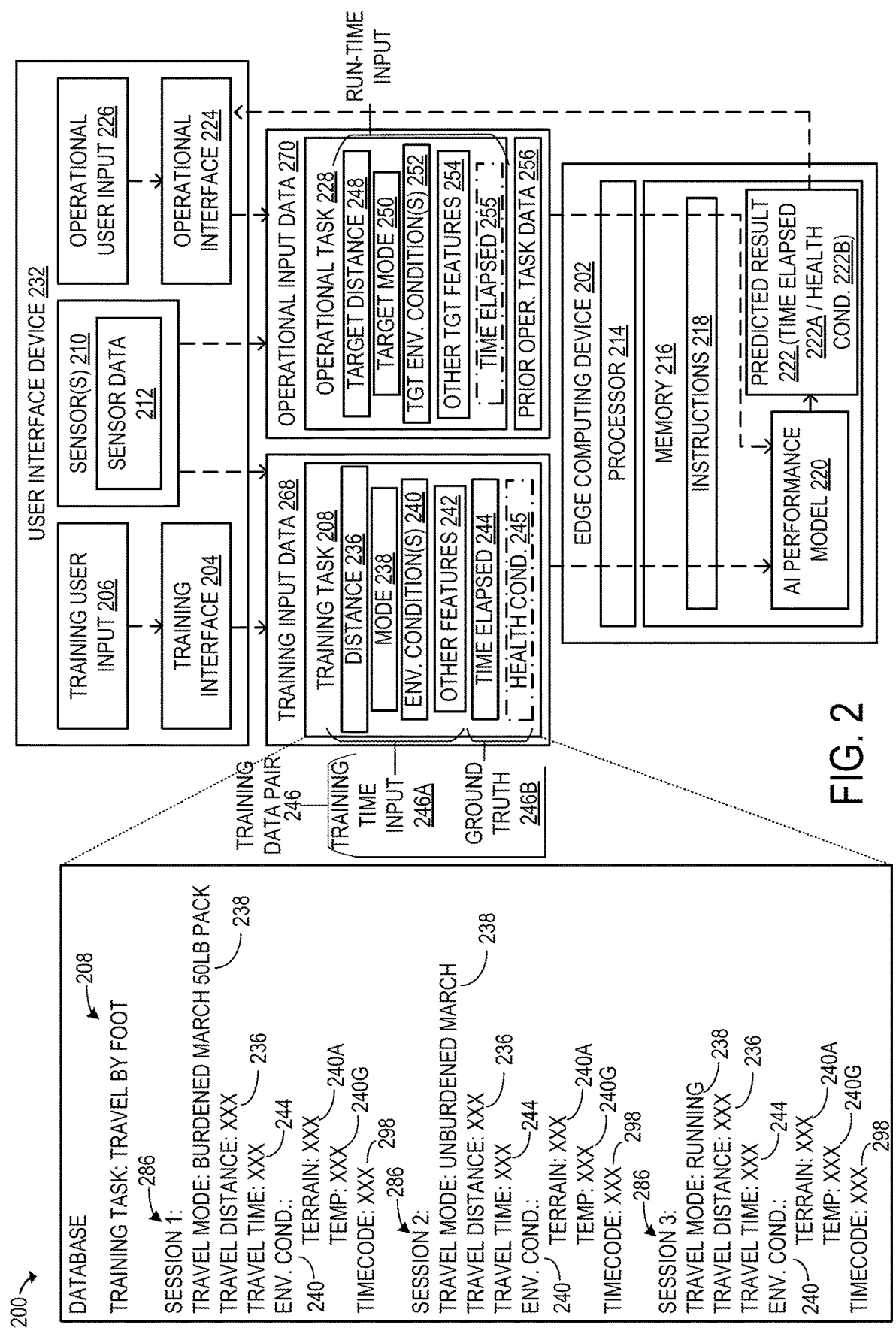
FIG. 2 shows a schematic diagram of an example system for determining a user's readiness for an operational task that may be used to infer a predicted result in the form of a predicted time elapsed for performance of an operational task or predicted health condition upon completion of the operational task, in the field environment of FIG. 1A, the field environment of FIG. 1B, or the field environment of FIG. 1C.

To address this challenge, and with reference now to FIG. 2, a system 200 is provided for determining a user's readiness for an operational task 228. The system 200 comprises an edge computing device 202. The edge computing device 202 is configured to receive training input data 268 during a training phase. As described in more detail below with reference to FIG. 5A, the training input data 268 includes, for each of a plurality of user training sessions 286 associated with a training task 208 performed by a user, a training data pair 246. The training data pair includes, as training-time input 246A, a distance of travel 236, a mode of travel 238, and one or more environmental conditions 240 in which the training task 208 is performed during the training session 286. The one or more environmental conditions 240 are selected from a plurality of predefined environmental conditions, examples of which are discussed below. The training data pair 246 also includes, as ground truth output 246B, a time elapsed 244 for performance of the training task by the user during the training session 286.

Figure 9:
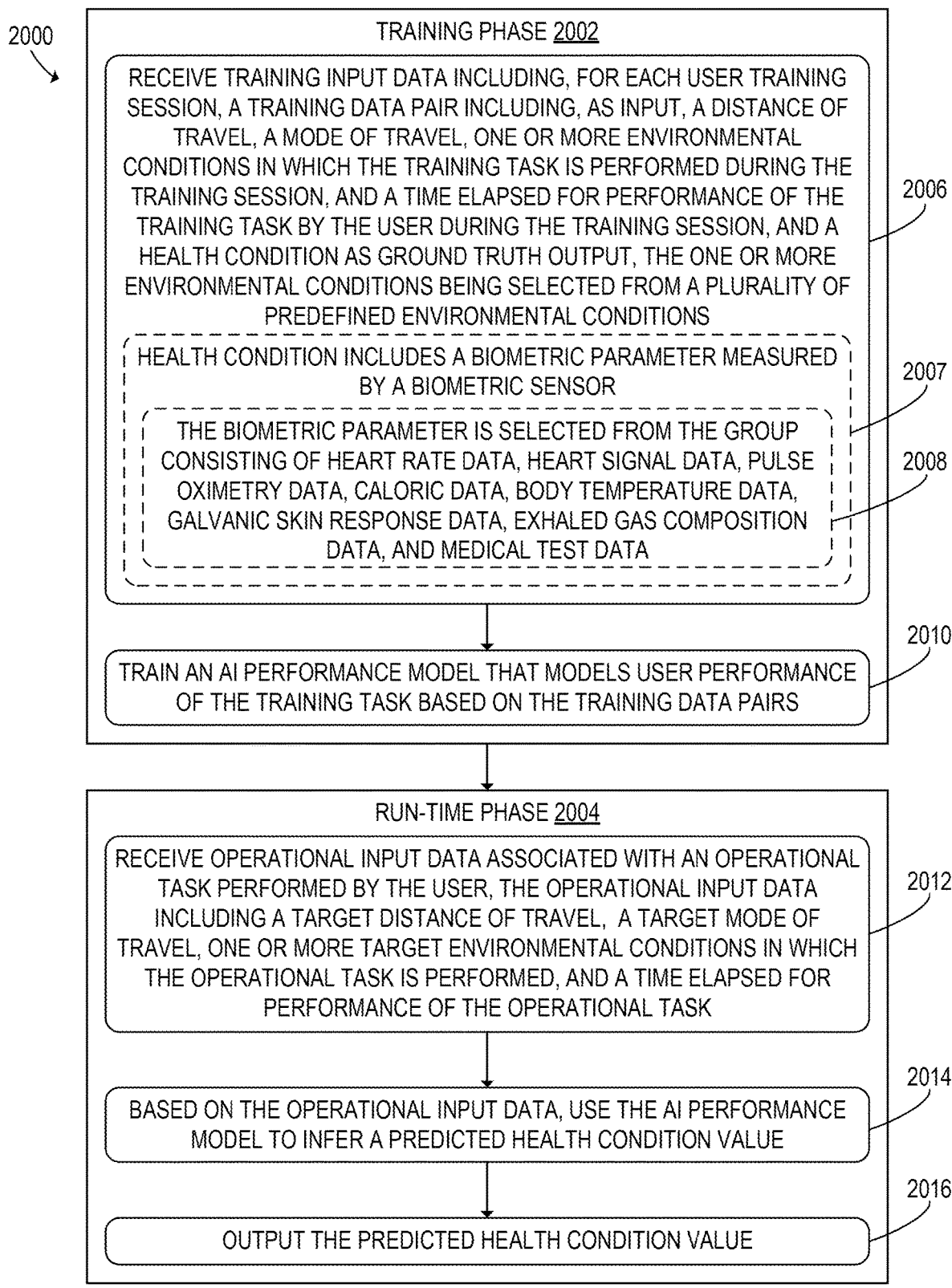
FIG. 9 shows a flowchart of another example method for determining a user's readiness for an operational task, according to one example embodiment.
Figure 10:
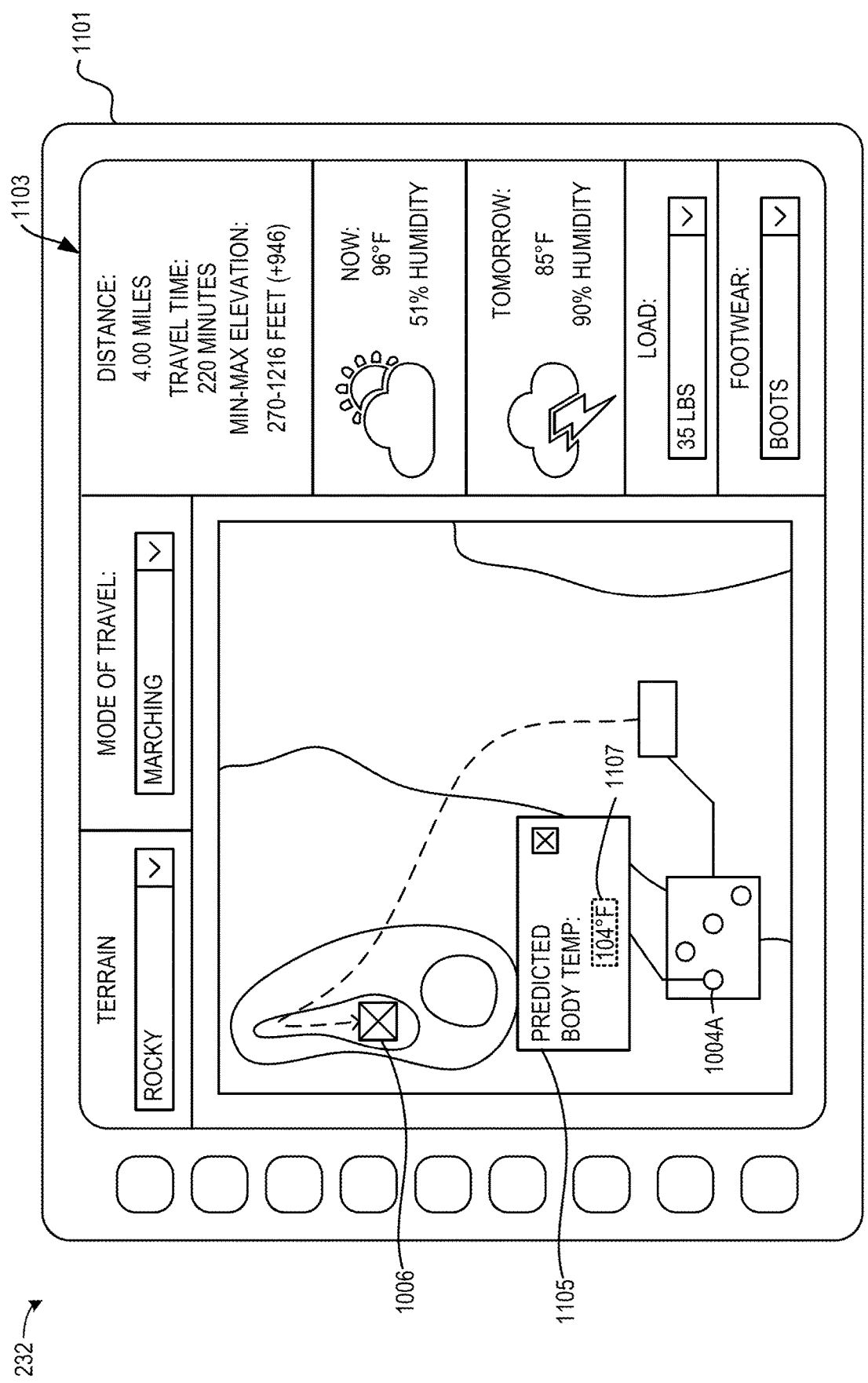
FIG. 10 shows a graphical user interface of an example of a computing device that may be used to determine a user's readiness for an operational task, according to one example embodiment.

The edge computing device 202 is a computing device having a position on a network topology between a local network (e.g., an ad hoc mesh network) and a wider area network (e.g., the Internet). The edge computing device 202 comprises a processor 214 and a memory 216 storing instructions 218 executable by the processor 214. Briefly, the instructions are executable to, during a training phase, receive the training input data 268 and to train an artificial intelligence (AI) performance model 220 that models user performance of the training task 208 based on the training data pairs 246. As described in more detail below with reference to FIGS. 5A and 5B, the AI performance model 220 is trained to infer a predicted result 222, which may be a predicted time elapsed 222A for performance of an operational task by the user, as illustrated in FIG. 4A through FIG. 8B or a predicted health condition 222B upon completion of the operational task 228 by the user, as illustrated in FIGS. 9 and 10.

Figure 5A:
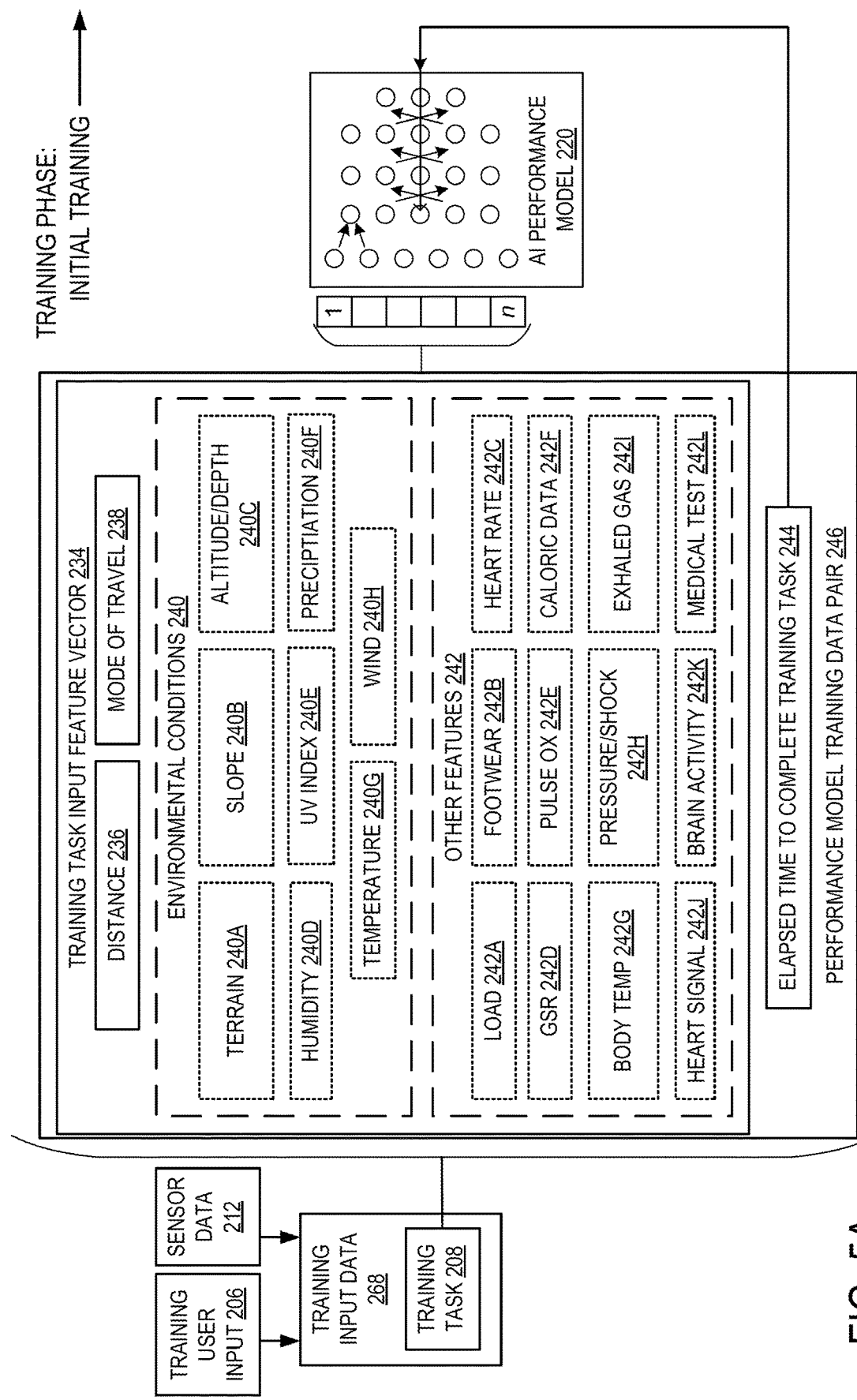
FIG. 5A shows an example of a training data pair for the system of FIG. 2.
Figure 5B:
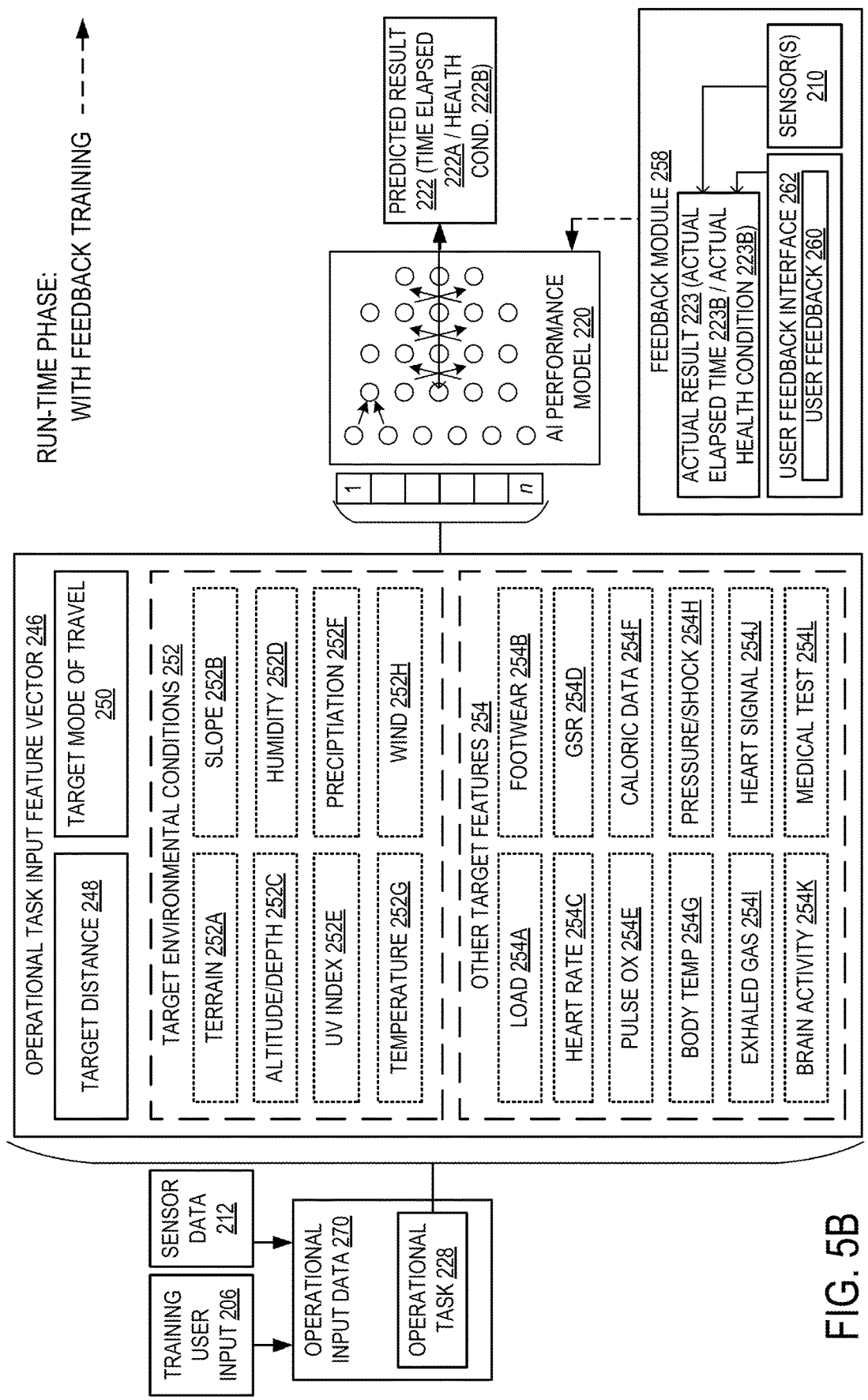
FIG. 5B shows an example of an operational task feature vector for the system of FIG. 2.
Figure 5C:
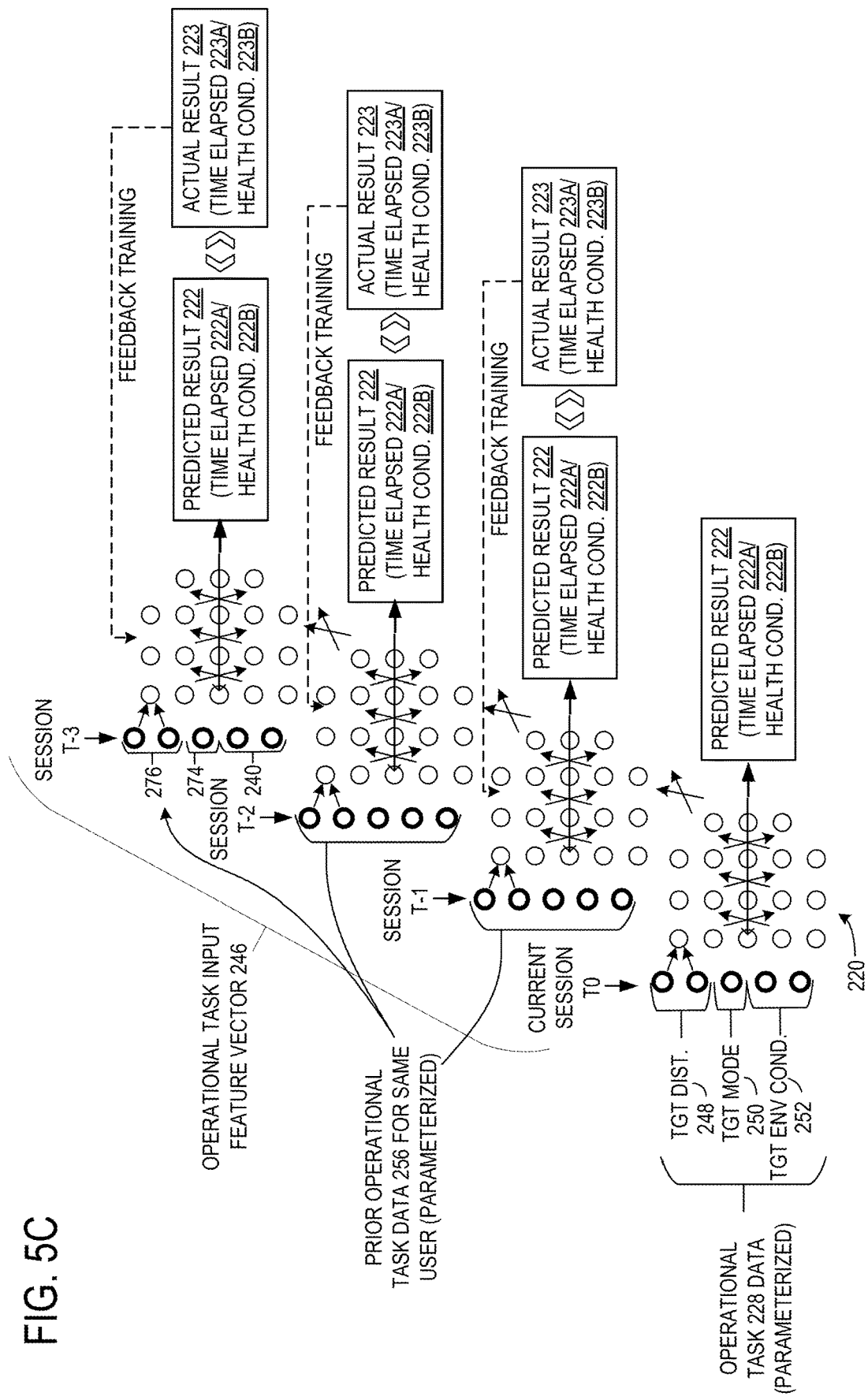
FIG. 5C shows an example operational task input vector for the system of FIG. 2 using a recurrent neural network as an AI performance model.

The edge computing device 202 is further configured to, during a run-time phase after training of the AI performance model 220 during the training phase, receive operational input data 270 associated with the operational task 228. As described in more detail below, the operational input data 270 includes an operational task 228, which in turn includes, a target distance of travel 274A, a target mode of travel 276A, and one or more target environmental conditions 278A in which the operational task 228 is performed. It will be noted that for the embodiment shown in FIGS. 9 and 10, in which training input data includes health condition 282 of a user upon completing a training task 208, the time elapsed for performance of an operational task 228 is included in the operational input data 270, and is used by the AI performance model 220 to predict a health condition 222B of the user upon completion of the operational task. The operational input data 270 may further including prior operational task data 299, which includes parameters 274A, 276A, 278A, and possibly 280A for prior sessions of operational tasks performed by the same user. As illustrated in FIG. 5C, the input vector provided to the AI performance model 220 for a particular user for a particular operational task can include an input subvectors for a current operational task 228, as well as input subvectors including parameterized data from one or more prior completed operational tasks by the same user (i.e., prior operational task data 299), illustrated at Session T-1, Session T-2, and Session T-3. Use of a recurrent neural network as the AI performance model 220 will enable the AI performance model 220 to weight connections between neurons of the layer of the network representing the current time step for a yet to be performed operational task 228, and prior completed operational tasks for which prior operational task data 299 is available, including both the inputs of travel mode 276, travel distance 274, and environmental conditions 278, but also the prior actual (measured) time elapsed data or health condition data. As shown in FIG. 5C, at each prior timestep, the actual measured result (time elapsed or health condition) may be used to perform feedback training of the AI performance model, as well.

Returning to FIG. 2, based on the operational input data 270, the trained AI performance model 220 is used to infer a predicted result 222 such as a predicted time elapsed 222A for performance of the operational task 228. The instructions 218 are further executable to output the predicted time elapsed 222A. In other examples, and as described in more detail below with reference to FIGS. 9 and 10, the operational input data 270 may alternatively include a time elapsed 280 for performance of the operational task, and the AI performance model may be trained to predict and output another parameter or condition associated with the operational task as the predicted result 222, such as a predicted health condition 222B of a user after performing the operational task.

In the example depicted in FIG. 2, the predicted time result 222 is output to a user interface device 232. The user interface device 232 may comprise a communication unit (e.g., a radio), a head-mounted display (HMD) device, a smart weapon, an in-field computing device (e.g., a smartphone, a tablet, or a laptop computing device), or a remote computing device (e.g., a workstation in a remote command center). It will also be appreciated that the user interface device 232 may comprise any other suitable device or combination of devices configured to perform the functions described herein. The user interface device 232 may be configured to display or otherwise present the predicted result 222 to a user via a display. In other examples, the predicted result 222 can be output to any other suitable device or combination of devices, such a computing device for downstream processing.

In some examples, at least a portion of the training input data 268 and/or the operational input data 270 is user input. For example, the user interface device 232 comprises a training interface 204 configured to receive a training user input 206 of the training task 208. The user interface device 232 further comprises an operational interface 224 configured to receive an operational user input 226 of the operational task 228. For example, a user may input the travel distance 236, travel mode 238, environmental conditions 240 or other features 242 of the training task 208, as well as the time elapsed for performance of the training task via a mobile computing device such as a smart phone.

In other examples, the training interface 204 and/or the operational interface 224 can be implemented at another suitable device. For example, the training interface 204 and/or the operational interface 224 can be implemented at the edge computing device 202. As another example, the training interface 204, the operational interface 224, and the edge computing device 202 can be implemented at separate devices. In one particular example, the edge computing device 202 may be incorporated into a wearable article, such as a uniform, helmet, glasses, weapon, tool, footwear, etc., and may be outfitted with sensors that capture the training time input 246A and ground truth input 246B during performance of the training task 208.

In yet other examples, and as described in more detail below, at least a portion of the training input data 268 and/or the operational input data 270 may comprise sensor data 212 received from one or more sensors 210 on the user interface device. For example, the user interface device may be a smart watch, smart phone or tablet computer carried during performance of the training task 208, and the sensors 210 may be a GPS and accelerometers contained within the smart watch, smart phone, or tablet computer. Information regarding the training task 208 and/or the operational task 228 may also be obtained from one or more purpose-built AI models. For example, a spiking neural network may be used to identify a task 208 or mode 238 from among a plurality of predefined tasks that it has been trained to recognize. Thus, the AI model may be configured to recognize foot travel vs. vehicular travel as different tasks, and further may be configured to recognize burdened marching, unburdened marching, running, and walking as modes of travel by foot, or may be configured to recognize driving by car, motorcycle, jeep, personnel carrier, or tank, as modes of vehicular travel. The one or more sensors 210 may be implemented at the user interface 232, as depicted in FIG. 2. It will also be appreciated that the sensors 210 may be implemented at any other suitable device or combination of devices.

Figure 3:
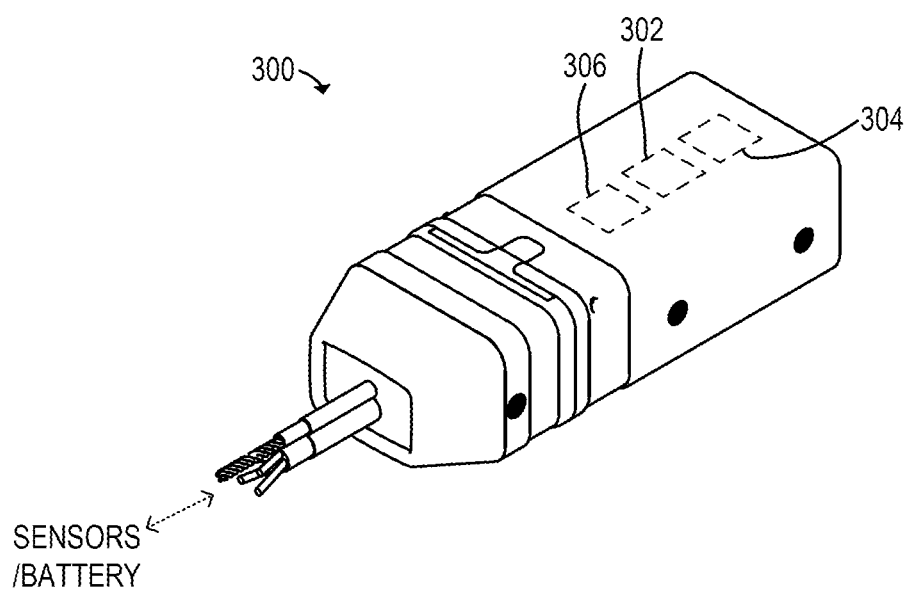
FIG. 3 shows one example of a computing device that may be used as the edge computing device of the system of FIG. 2.

FIG. 3 shows one example of a computing device 300, which may be configured to enact at least a portion of the methods disclosed herein. For example, the computing device 300 can serve as the edge computing device 202 of FIG. 2.

The computing device 300 comprises a processor 302 and a memory 304. In some examples, the computing device 300 further comprises at least one sensor 306. The at least one sensor 306 is an example implementation of the one or more sensors 210 of FIG. 2. Some examples of suitable sensors include an inertial measurement unit (IMU), a global positioning system (GPS) sensor, an altimeter, a pressure sensor, a force sensor, an antenna, a thermometer, a heart rate monitor, a pulse oximeter, a skin galvanometer, and a breath gas analyzer. The at least one sensor 306 can additionally or alternatively include any other suitable device or devices. Computing device 300 is typically of a compact size and can be incorporated into a wearable device, article of clothing, or equipment such as a weapon or tool, for example. The wires extending from the device may be attached to a wiring harness that may extend to sensors and/or a battery positioned throughout wearable device, article of clothing, weapon, or tool, for example.

Figure 4A:
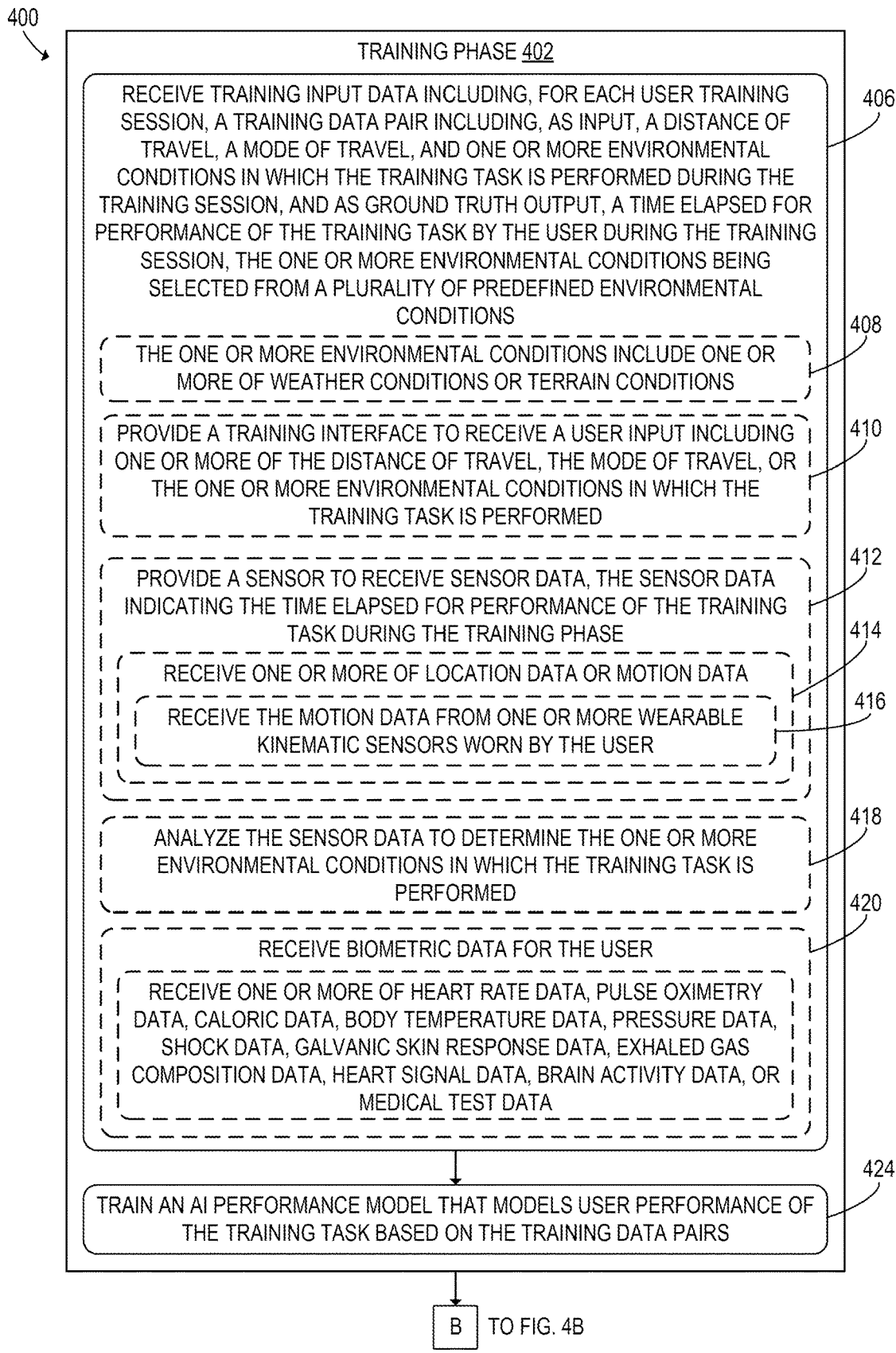
FIGS. 4A and 4B show a flowchart of an example method for determining a user's readiness for an operational task, according to one example embodiment.

With reference now to FIG. 4A, a flowchart is illustrated depicting an example method 400 for determining a user's readiness for an operational task. The following description of method 400 is provided with reference to the software and hardware components described above and shown in FIGS. 1-3 and 5-8, and the method steps in method 400 will be described with reference to corresponding portions of FIGS. 1-3 and 5-8 below. It will be appreciated that method 400 also may be performed in other contexts using other suitable hardware and software components.

It will be appreciated that the following description of method 400 is provided by way of example and is not meant to be limiting. It will be understood that various steps of method 400 can be omitted or performed in a different order than described, and that the method 400 can include additional and/or alternative steps relative to those illustrated in FIGS. 4A and 4B without departing from the scope of this disclosure.

Figure 4B:
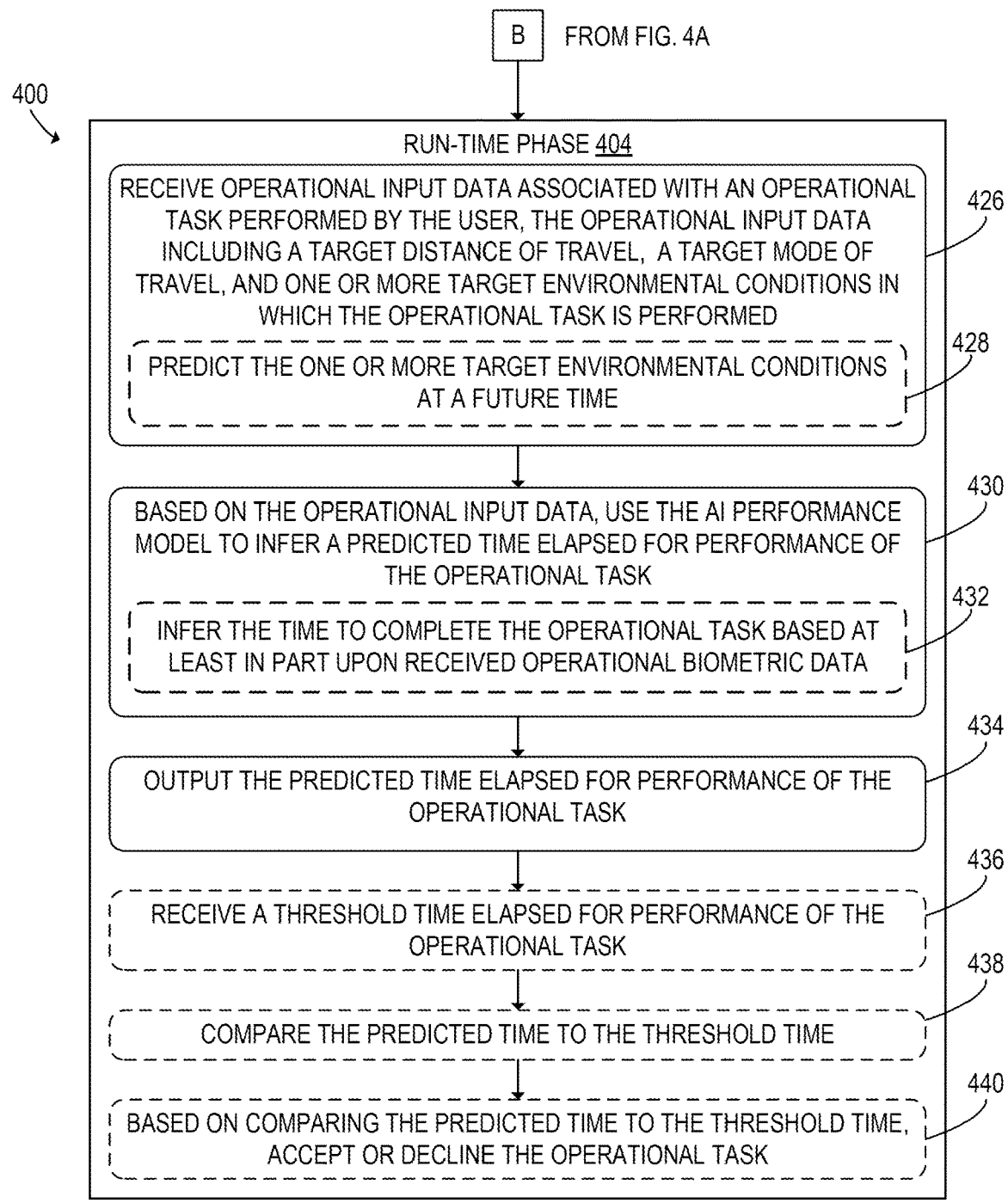

The method 400 includes a training phase 402, illustrated in FIG. 4A, and a run-time phase 404, illustrated in FIG. 4B. In some examples, the training phase 402 occurs in a training environment and the run-time phase 404 occurs in a deployed operational field environment. For example, the training phase 402 may occur while the soldiers 1004 of FIG. 1A are in a field training exercise (FTX) or military training school, and the run-time phase 404 may occur while the soldiers 1004 are deployed in the field environment 1000. As another example, the training phase may occur while the firefighters 1010 of FIG. 1B are in a fire academy or training class, and the run-time phase may occur while the firefighters 1010 are working in the field environment 1008. As yet another example, the training phase may occur while the user 1016 of FIG. 1C is running in a training environment, and the run-time phase may occur during a competition.

In other examples, at least a portion of the training phase 402 and the run-time phase 404 may occur concurrently or in the same environment. For example, the performance model 220 of FIG. 2 may comprise a continual learning model that can learn and adapt during the run-time phase, based on feedback received from the user.

Continuing with FIG. 4A, at 406 the method 400 comprises, during the training phase, for each of a plurality of user training sessions 286 associated with a training task 208 performed by a user, receiving training input data 268. FIG. 2 shows one example of a database storing data collected during the training phase for a training task 208 of travel by foot. Three training sessions 286 are illustrated: Session 1, Session 2, and Session 3, although it will be appreciated that thousands or even millions of such sessions may be recorded in practice. Training input data 268 may be received from training interface 204 and/or sensors 210 at step 402 and stored in a database record for each session 268. The database record for each session includes data indicating a travel mode 238, travel distance 236, time elapsed 244 for travel, and environmental condition(s) 240, including terrain 240A and ambient temperature 240G. A timecode 298 data entry is also included indicating the date and time at which each session took place. In the embodiment of FIGS. 9 and 10, used to predict a predicted health condition 222B, a health condition 245 may be included in the training data pair 246 as ground truth 246B rather than elapsed time 244 being included as ground truth 246B. The health condition 245 may be, for example, a core body temp, diagnosed condition such as heatstroke, etc. In the illustrated example, the mode of travel 238 for session one is a burdened march with a 501b pack (e.g., as depicted in FIG. 1A), the mode of travel 238 for session two is an unburdened march during firefighting (e.g., as depicted in FIG. 1B), and the mode of travel 238 for session three is running (e.g., as depicted in FIG. 1C).

With continued reference to FIG. 4A, as briefly discussed above, the training input data 268 includes, for each user training session 286, a training data pair 246. The training data pair 246 includes, as training-time input 246A, a distance of travel 236, a mode of travel 238, and one or more environmental conditions 240 in which the training task 208 is performed during the training session 286. The one or more environmental conditions 240 are selected from a plurality of predefined environmental conditions, examples of which are discussed below in relation to FIG. 5A. The training data pair 246 includes, as ground truth 246B output, a time elapsed 244 for performance of the training task by the user during the training session, or a health condition 245 as described above (with the time elapsed 244 being included in the training-time input 246A when the health condition 245 is used as ground truth 246B). The distance of travel 236, the mode of travel 238, and the set of environmental conditions 240 can be used to form a training task input feature vector 234 for the AI performance model 220 during training, as depicted in FIG. 5A.

The training task input feature vector 234 includes parameterized representations of the distance 236 of travel and the mode 238 of travel. For example, and with reference now to FIG. 1C, the training task may comprise a road run with a set distance (e.g., five miles). In this example, the distance 236 of the training task input feature vector 234 of FIG. 5A corresponds to the distance of the road run (e.g., five miles), and the parameterized representation of the mode 238 of travel indicates that the mode is running.

Continuing with FIG. 5C, the training task input feature vector 234 may also include one or more environmental conditions 240 indicating the one or more environmental conditions under which the training task is performed. Referring to FIG. 4A, at 408, the one or more environmental conditions 240 may include one or more of weather conditions 252A such as temperature, wind, humidity, precipitation, UV index, etc., or terrain conditions such as ground surface type (muddy, hardpack, loose gravel, rocky, sandy, grass field, forest floor, asphalt, concrete, dirt trail, running track, etc.). As one specific example, the one or more environmental conditions may include rainy weather and muddy terrain. As another specific example, the one or more environmental conditions may include sunny weather and dry, rocky terrain. Although these example sets of environmental conditions comprise two types of conditions (e.g., weather conditions and terrain conditions), it will also be appreciated that the one or more environmental conditions under which the training task is performed may include any other suitable number of environmental conditions.

The environmental conditions 240 of the training task input feature vector 234 may include a terrain feature 240A, a slope feature 240B, an altitude and/or depth feature 240C, a humidity feature 240D, an ultraviolet (UV) index feature 240E, a precipitation feature 240F, a temperature feature 240G, wind speed and direction vector 240H, and/or any other suitable feature or features. These features are parameterized in the input vector, for example, as values between zero and one, inclusive. In this manner, the training task input feature vector 234 may represent the weather conditions, terrain conditions, and/or any other suitable environmental conditions under which the training task is performed.

In some examples, the terrain feature 240A may be represented as a coefficient of friction indicating a level of difficulty associated with traveling though the training environment. For example, it may be more difficult for the soldiers 1004 of FIG. 1A to traverse a sandy trail than an asphalt road. Accordingly, the terrain feature 240A may comprise a higher coefficient of friction (e.g., 0.9 in a normalized range of [0-1]) for the sandy trail and a lower coefficient of friction (e.g., 0.1 in the normalized range of [0-1]) for the asphalt road. While the examples of FIGS. 1A-C depict various users traveling over land, it will also be appreciated that the terrain feature 240A and any other suitable feature or features may describe a task carried out in other environments. For example, a measure of wave height, turbulence, and/or current may be used to represent a user swimming through rough or calm standing or flowing water.

The training task input feature vector 234 may additionally or alternatively include one or more other features 242 that can affect the user's performance. Any suitable and parameterizable feature or features may be included in other features 242. As described in more detail below, some examples of suitable features include a load 242A (e.g., rucksack weight), a type of footwear 242B (e.g., combat boots or running shoes), heart rate data 242C (e.g., a user's current heart rate, maximum heart rate, a time at the user's maximum heart rate, and/or resting heart rate), a user's galvanic skin response (GSR) 242D (e.g., a measure of how much the user is sweating), pulse oximetry data 242E, caloric data 242F (e.g., calories burned by the user), body temperature data 242G, pressure and/or shock data 242H (e.g., representing an impact or G-force experienced by the user), exhaled gas composition data 242I, heart signal (e.g., electrocardiogram) data 242J (e.g., waveform components), brain activity 242K (e.g., encephalogram data), and medical test data 242L (e.g., blood test data).

It will be appreciated that the particular set of features included in the training task input feature vector 234 during the training phase will be included for each and every training session, and will also be included in the input vector in the run time phase, with the presence of each condition indicated on a normalized scale of zero to one. Thus, if fitness is being measured for two different environmental conditions that may be present in one session but not present in another session, then entries in the training task input feature vector 234 will be included for each of these two different environmental conditions in each of the training sessions, and when an environmental condition is not present in one of the sessions, it will be indicated as zero.

The training task input feature vector 234 is paired with a time elapsed 244 (or alternatively with a health condition 245) associated with the performance of the training task to form a performance model training data pair 246. For example, referring again to FIG. 1C, a performance model training data pair for the runner 1016 includes the time for the user to perform her training run (e.g., 40 minutes). The time elapsed 244 is typically measured programmatically by sensors 210 monitoring the performance of the user during the training session, or is manually input by the user or other operator of the system after the training session. Likewise, when the health condition 245 is used as ground truth, the time elapsed can be included as training time input 246A and the health condition 245 can be entered by the user or other professional, based on sensor data 212, personal observation, etc.

Accordingly, the performance model training data pair 246 may be populated based upon a training user input 206 that is entered by the user via a training interface 204. With reference again to FIG. 4A, at 410, the method 400 may include providing a training interface to receive a user input including one or more of the distance of travel, the mode of travel, or the one or more environmental conditions in which the training task is performed. Returning to FIG. 2, for example, the distance 236, mode of travel 238, one or more environmental conditions 240, and/or one or more other features 242 may be input as training user input 206 via the training interface 204 of the user interface device 232 at step 410 of method 400.

Figure 6B:
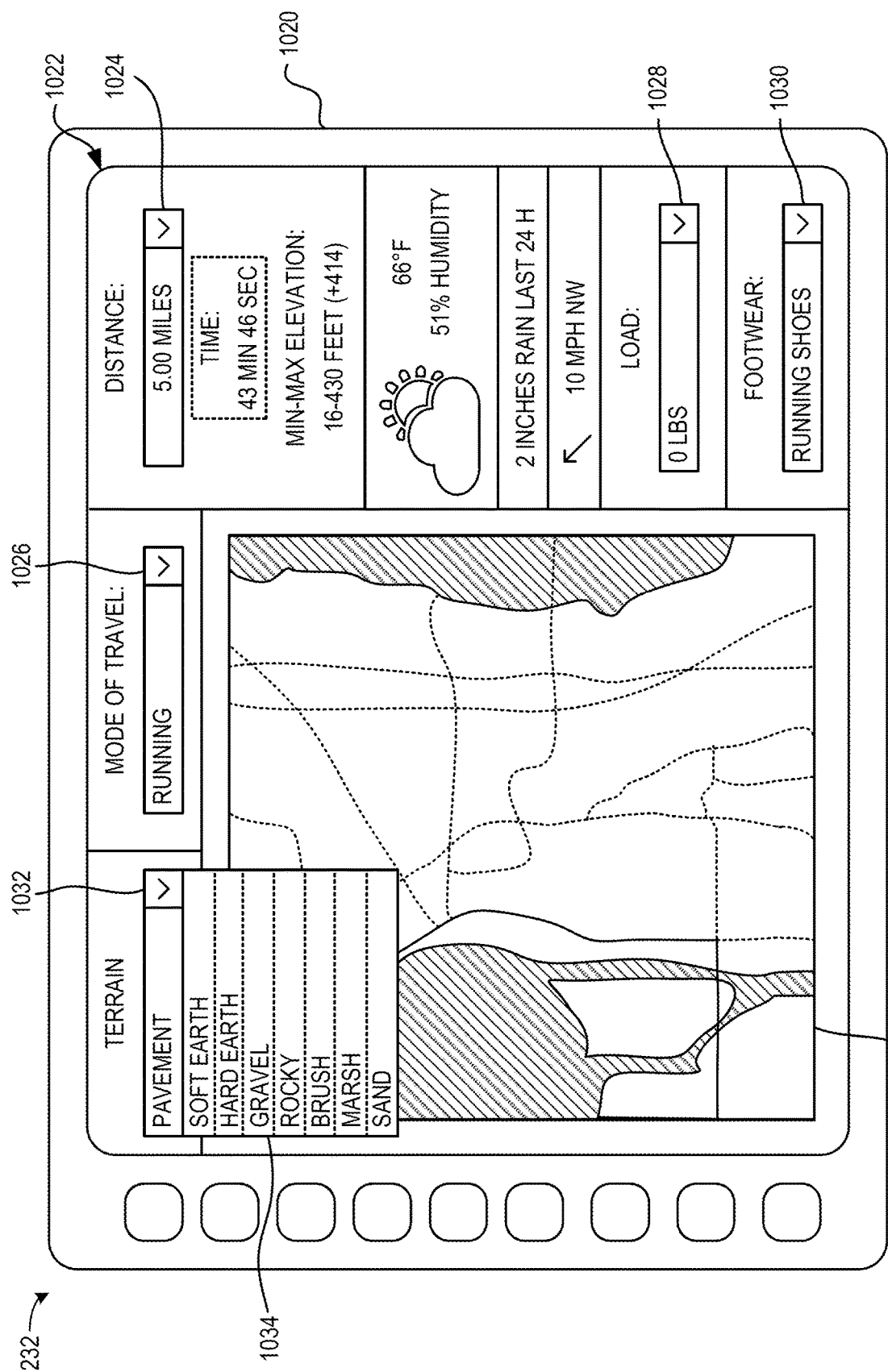

Examples of the training interface 204 of the user interface device 232 of FIG. 2 are illustrated in FIGS. 6A-6B. These figures depict one example of a user computing device in the form of a tablet computing device 1020 that can be used as the user interface device 232, for example, in the field environments of FIGS. 1A-1C. In some examples, the tablet computing device 1020 is operated by the user 1016 of FIG. 1C. In other examples, the tablet computing device 1020 can be monitored by another user who is either in the field environment 1014 or at a remote location.

In the example of FIG. 6A, the tablet computing device 1020 displays a graphic user interface (GUI) 1022 for a land-based training task comprising a five-mile run. The GUI 1022 includes user-operable selection features configured to receive user-input data. The user input data may include the distance, mode of travel, and an indication of the conditions under which the training task is accomplished. For example, the GUI 1022 includes a distance selector 1024 for a user to input a length of the training run and a mode of travel selector 1026 for the user to input the mode of travel (e.g., running). The GUI 1022 also includes a load selector 1028 for the user to indicate any load being carried during the training task (e.g., weights or a rucksack), a footwear selector 1030 to indicate a type of footwear used during the training task (e.g., running shoes), and a terrain selector 1032 to indicate a type of terrain traversed during the training task (e.g., soft or hard earth, rocky terrain, brush, marshy, etc.). The load selector is set to zero, which indicates a travel mode of unburdened run. If the user selects a positive load weight via load selector 1028, the mode selector 1026 is configured to automatically change to indicate a mode of "burdened run." It will be appreciated that the AI performance model is typically trained for a particular task, such as travel by foot in the examples discussed thus far. Thus, all of the modes of travel available in selector 1026 are modes of traveling by foot. The user-input data provided via the GUI 1022 are translated into one or more values that are used to populate the training task input feature vector 234. In other examples, the task may be more broadly defined as "human powered travel" and a predefined set of different cross training activities may be defined as the modes of travel in training input data 268 for the AI performance model 220. For example, the modes 238 of travel may be defined as swimming, cycling, and running; rowing and running; or swimming and cycling. In this way, fitness in a plurality of different forms of activity may be correlated with each other, and may be used to predict user performance in any one of the activities.

In some examples, the conditions specified by the training task input feature vector are predefined. The predefined terrain types may be user-specified or determined programmatically. For example, the terrain types may be programmatically extracted by analyzing a map 1036 of the training environment 1014.

FIG. 6B depicts several examples of predefined terrain types for the training task. In FIG. 6B, the terrain selector 1032 is depicted as a drop-down menu 1034 comprising a list of predefined terrain types (e.g., pavement, soft earth, hard earth, gravel, rocky terrain, brush, marsh, and sand). It will also be appreciated that the list of predefined terrain types may include any other suitable types of terrain. Each of the predefined terrain types is associated with a value for the terrain feature 240A (e.g., in a lookup table). Accordingly, a user selection of a terrain type can be translated into a value that is used to populate the training task input feature vector 234.

In the above examples, the performance model training data pair 246 is populated based upon user actuation of one or more GUI elements. It will also be appreciated that the user input may be provide in any other suitable manner. For example, the training interface 204 may comprise a natural language interface configured to extract the training user input 206 from a user's speech. For example, the user may say "five-mile run, begin," prior to initiating a training task. A natural language processing algorithm can be used to extract the distance 236 and the mode of travel 238 from the user's speech.

Referring again to FIG. 4A, the method 400 includes, at 412, providing a sensor to receive sensor data. Sensors 210 are generally in FIG. 2, and sensor data generally indicated at 212 in FIG. 2. In some examples, the sensor data 210 may be received from one or more local sensors 210 in the computing device, such as user interface device 232. For example, when the computing device 300 of FIG. 3 is used as user interface device 232, the computing device 300 may receive the sensor data 212 from a sensor 306 integrated within the device 300. In other examples, the sensor data 212 may be received from one or more remote sensors, or from a combination of at least one local sensor and at least one remote sensor.

One or more parameters of the performance model training data pair 246 can be populated based upon the sensor data 212. For example, as indicated at 412 of FIG. 4A, the sensor data indicates the time elapsed for performance of the training task during the training phase. In some examples, receiving the sensor data comprises receiving one or more of location data or motion data (e.g., position, velocity, and/or acceleration data) of the user, as indicated at 414, which can be used to monitor the user's progress on the training task. For example, and with reference again to FIG. 6A, the sensor data 212 may indicate a time 1038 (e.g., 43 minutes and 46 seconds) to perform the five-mile run.

Figure 7:
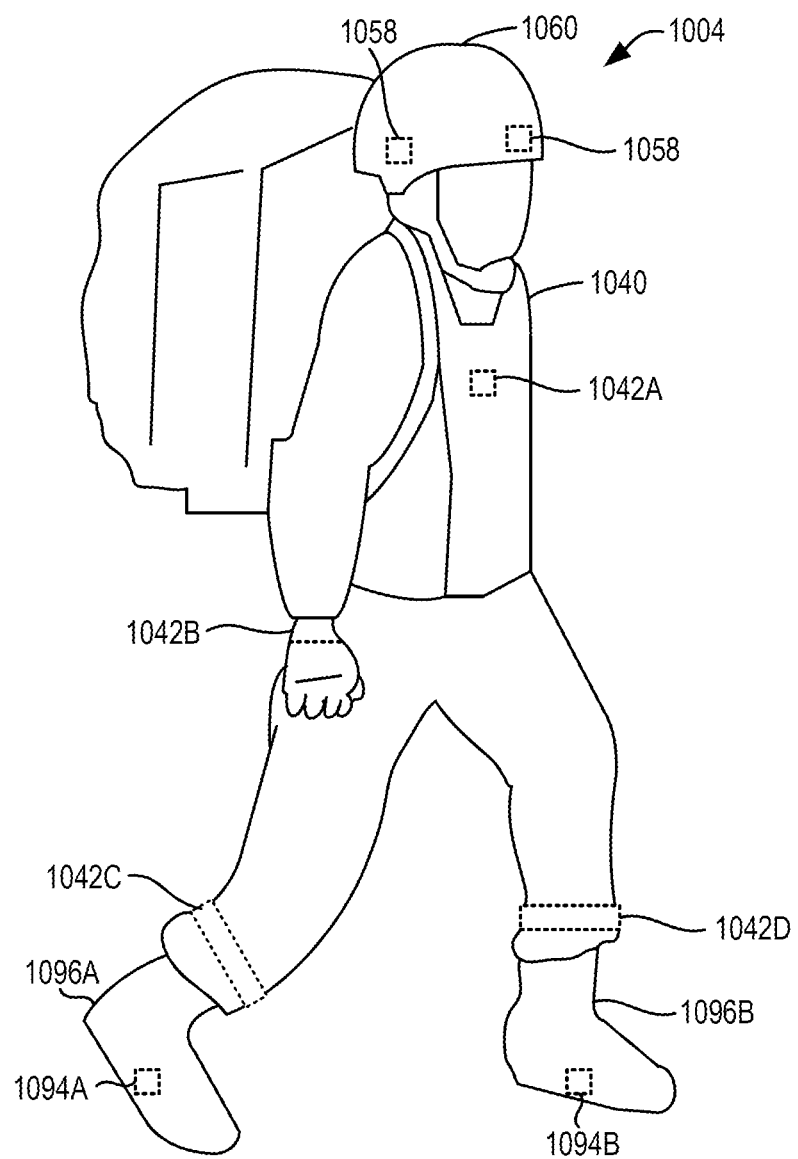
FIG. 7 shows an example of one or more sensors that can be used in the field environment of FIG. 1A.

In some examples, at 416 of FIG. 4A, receiving the sensor data may further comprise receiving the motion data from one or more wearable kinematic sensors worn by the user. For example, FIG. 7 shows one of the soldiers 1004 of FIG. 1A wearing a uniform 1040 comprising a plurality of embedded motion sensors (e.g., IMUs) 1042A-D. The motion sensors 1042A-D are configured to monitor the relative positions of different parts of the soldier's body (e.g., hands, legs, torso), which can indicate the user's progress through a defined sequence of movements (e.g., an exercise or a battle drill).

Referring again to FIG. 4A, at 418, the sensor data may include terrain-related data and/or weather data, discussed above, which can be analyzed to determine under which of the plurality of defined sets of environmental conditions the training task is accomplished. For example, the tablet computing device 1020 may receive and display weather data 1044 that is received from or derived from weather sensor data 212 (e.g., data from a barometer, a thermometer, a hygrometer, a rain sensor, and a wind sensor). The weather data 1044 comprises data indicating a current weather condition (e.g., partly cloudy as indicated by icon 1046), temperature data 1048 indicating a current temperature (e.g., 66° F.), humidity data 1050 indicating a current relative humidity (e.g., 51%), precipitation data 1052 indicating an amount of precipitation (e.g., 2 inches of rain in the last 24 hours), wind data indicating a wind direction (e.g., northwest) as illustrated by icon 1054, and wind speed data 1056 indicating wind speed and direction (e.g., 10 miles per hour northwest). One or more of these weather data 1044 may be parameterized for inclusion in the training task input vector 246.

Referring again to FIG. 4A, at 420, receiving the sensor data may comprise receiving biometric data for the user. The biometric data may encode information regarding a user's exertion, fatigue, susceptibility to heat injury, etc. For example, receiving the biometric data may include receiving one or more of heart rate data, pulse oximetry data, caloric data, body temperature data, pressure data, shock data, galvanic skin response data, exhaled gas composition data, heart signal data, brain activity data, or medical test data.

As one example, a heart rate monitor worn by the user may indicate the intensity of a training exercise, which can be encoded in the heart rate feature 242C of the training task input feature vector 234. A GSR sensor can be used to infer the user's stress level. A pulse oximeter can indicate a user's blood oxygen level, which affects physical performance and can be encoded in the pulse oximetry feature 242E. As another example, a breath gas analyzer can be employed to determine the concentration of various gases in the user's exhaled breath, which can indicate changes in the user's biochemistry during performance of the training task (e.g., indicating that the user has begun burning fat) that can be encoded in the exhaled gas feature 242I. Each of these data can be included in the training task input feature vector 234. In this manner, the performance model 220 can be trained to infer based upon a user's exertion, stamina, fatigue, etc. how much time it may take for the user to perform a task.

Pressure/shock data 242H may also have health and performance implications. In the example of FIG. 7, one or more force sensors 1058 may be worn by one of the soldiers 1004 to obtain pressure/shock data. For example, the one or more force sensors 1058 may be embedded in a helmet 1060 of the soldier 1004 to determine if the soldier 1004 has experienced a concussive impact (e.g., from a blow to the head or a shock wave from an explosive detonation) which can affect the soldier's ability to perform a task. Accordingly, pressure/shock data 242H may be included in training task input feature vector 234.

Referring again to FIG. 2, two or more inputs of the training task input feature vector 234 may be correlated. For example, when the weather is hot and dry (e.g., as indicated in the temperature feature 240G and the precipitation feature 240F), the terrain (e.g., as indicated by the terrain feature 240A) may be sandy. When the weather is wet, the terrain may be muddy. As another example, a user's blood oxygen level (e.g., as determined via a pulse oximeter) may be correlated with lung capacity, which can be more difficult to measure. Establishing these correlations can reduce the number of user or sensor-provided inputs used to populate an input feature vector (e.g., the training task input feature vector 234) and can provide additional information for the performance model 220 that may not be explicit in the user input 206 or the sensor data 212. Further, the AI performance model may be equipped with one or more convolutional layers that enable the model to simplify such potentially correlated feature inputs, thereby increasing the efficiency of training the model.

Values within the feature vector may be normalized or scaled based on their respective input types. For example, for a distance 236 comprising values in a range of 0-100 km, a reported value of 20 km may correspond to 0.2 for a normalized range [0-1] for that input type. Each of a plurality of defined modes of travel are also assigned a value in the range of [0-1]. For example, running may be assigned a value of zero and marching may be assigned a value of one. Other modes of travel (e.g., cycling, swimming, crawling) may be assigned decimal values between zero and one (e.g., 0.1, 0.2, 0.3). In this manner, each input may be normalized or scaled to a normalized range of [0-1] that can be provided to the performance model 220. As described in more detail below, the model 220 may similarly output normalized or scaled inference values.

Next, at 424, the method 400 includes, based on the training task and the sensor data, training an AI performance model 220 for the user. The performance model 220 is trained to model user performance of the training task based on the training data pairs. Typically, a multitude of such training data pairs 246 are supplied, such as thousands or millions of such pairs. In this manner, the performance model 220 can learn an individual's performance capabilities in a variety of conditions for a given task, and learn to infer a predicted result 222, such as a predicted time elapsed 22A or predicted health condition 222B, based on run-time input conditions for the task.

In some examples, the performance model 220 can be trained at the edge computing device 202. In other examples, the edge computing device 202 can offload at least a portion of the training to one or more remote computing devices, such as servers in a data center.

The performance model 220 may be trained for a specific user over time. For example, a computing device (e.g., the edge computing device 300 of FIG. 3) can be assigned to one of the soldiers 1004 of FIG. 1A during entry-level military training, upon assignment to the team 1002, etc. The computing device may follow the soldier through their career. As another example, a computing device can be assigned to the firefighters 1010 of FIG. 1B upon joining a firefighting organization or during firefighter training. As yet another example, a computing device can be assigned to the runner 1016 of FIG. 1C upon joining an athletic organization.

In this manner, the device may monitor the user's experience over time. For example, the device may collect data over one year (or any other suitable duration) of training and learn how the user behaves under different conditions. This information can be used to identify conditions that correspond to training tasks not being met within a specified scope, such as being accomplished within a threshold time.

The device may further aggregate data over a longer duration (e.g., 30 years) of training and/or operation. In this manner, the device can be used to identify trends in the user's performance over time, such as one or more periods of improvement or decline, or signs of accumulating injury (e.g., sports injuries).

Referring now to the run-time phase 404 in FIG. 4B, the method 400 includes, at 426, receiving, at run-time, operational input data 270 associated with an operational task performed by the user, the operational input data 270 including a target distance 248 of travel, a target mode 250 of travel, and one or more target environmental conditions 252 or other target features 242 in which the operational task 228 is performed. Parameterized and normalized representations of the target distance 248 of travel and the target mode 250 of travel can be used to form an operational task feature vector 264 for the performance model 220, as depicted in FIG. 5B.

The operational task feature vector includes the target distance of travel 248 and the target mode of travel 250. For example, in FIG. 1A, the operational task may comprise a ruck march with a set endpoint (e.g., hilltop 1006). In this example, the distance 248 of the operational task feature vector 264 of FIG. 5B corresponds to the distance of the march (e.g., four miles), and the mode of travel 250 is marching.

The operational task feature vector 264 may also include one or more target environmental conditions 252 indicating the set of environmental conditions under which the operational task is expected to be performed. The target environmental conditions 252 of the operational task feature vector 264 correspond to the environmental conditions 240 of the training task input feature vector 234 of FIG. 5A, and include a terrain feature 252A, a slope feature 252B, an altitude and/or depth feature 252C, a humidity feature 252D, a UV index feature 252E, a precipitation feature 252F, a temperature feature 252G, wind speed and direction vector 252H, and/or any other suitable feature or features. In this manner, the operational task feature vector 264 may represent the weather conditions, terrain conditions, and/or any other suitable environmental conditions under which the operational task is performed. As discussed above, the format of the training task input feature vectors 234 used to train the AI performance model 220 and the operational task input feature vector 246 are typically the same, such that they include input data of the same type in the same location within the vector.

The operational task feature vector 264 may additionally or alternatively include other target features 254 that can affect the user's performance. The other target features 254 correspond to the features 242 of the training task input feature vector 234 of FIG. 5A, including a load 254A, a type of footwear 254B, heart rate data 254C, a user's GSR 254D, pulse oximetry data 254E, caloric data 254F, body temperature data 254G, pressure and/or shock data 254H, exhaled gas composition data 254I, heart signal data 254J, brain activity 254K, and/or medical test data 254L.

In some examples, the operational task feature vector 264 is populated based upon the operational user input 226. For example, the target distance 248, target mode of travel 250, one or more target environmental conditions 252, and/or one or more other target features 254 may be input by a user as user input 226 via the operational interface 224 of the user interface device 232, as shown in FIG. 2.

Figure 8A:
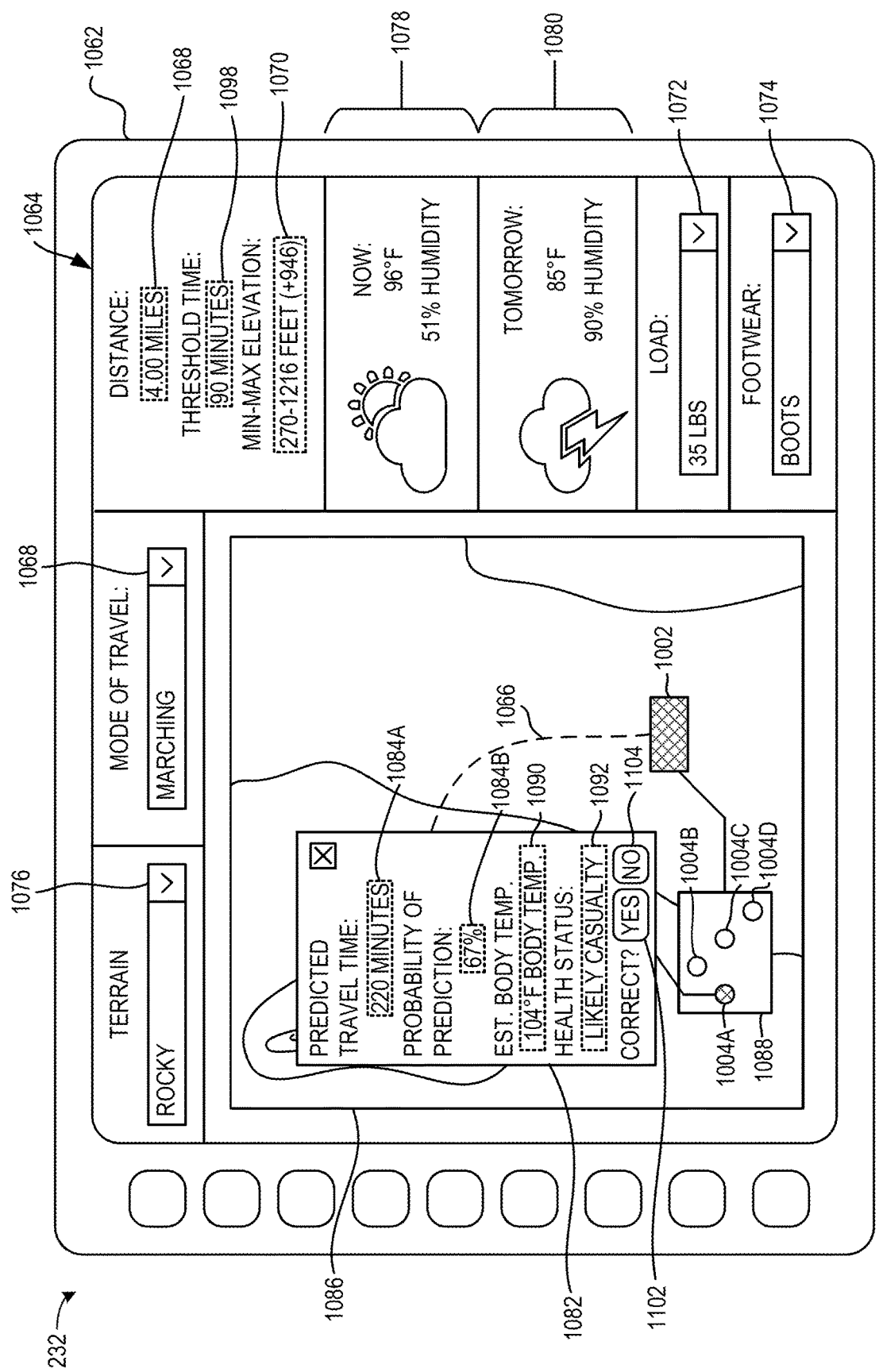
FIGS. 8A-8B show graphical user interfaces of an example of a computing device that may be used in the field environment of FIG. 1A or remotely therefrom.
Figure 8B:
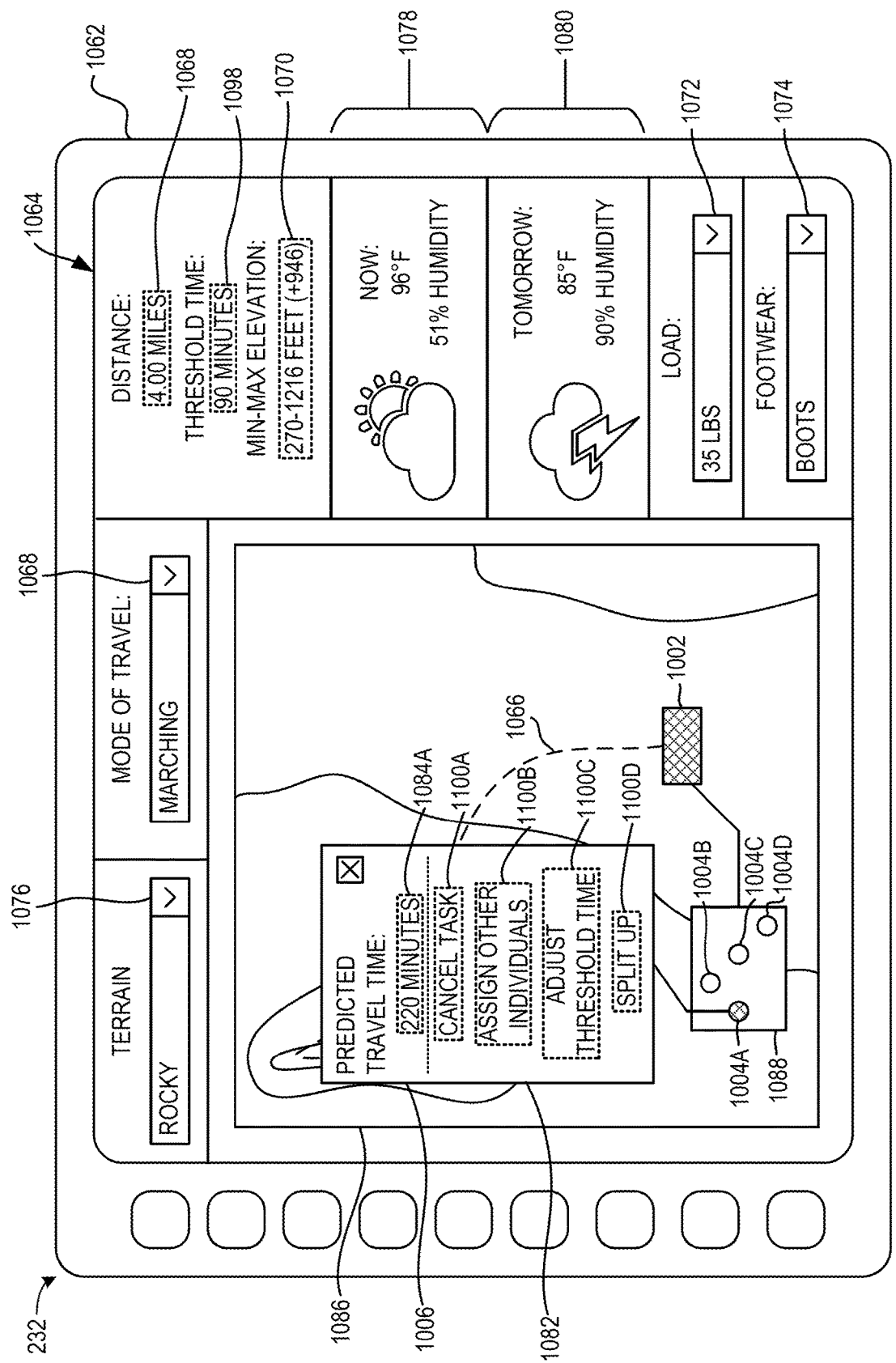

FIG. 8A depicts one example of a user computing device in the form of a tablet computing device 1062 that can be used in the environment 1000 of FIG. 1A. In some examples, the tablet computing device 1062 is operated by one of the soldiers 1004 of FIG. 1A. In other examples, the tablet computing device 1062 can be monitored by another user who is either in the operational environment 1000 or at a remote location. The tablet computing device 1062 is an example implementation of the user interface device 232 of FIG. 2.

In the example of FIG. 8A, the tablet computing device 1062 displays a GUI 1064 for a land-based operational task comprising a four-mile march to the hilltop 1006. The GUI 1064 includes user-operable selection features configured to receive user-input data. The user input data may include the distance, mode of travel, and an indication of the conditions under which the operational task is accomplished. For example, the user may input a route 1066 to the hilltop 1006 by drawing the route 1066 on a touch-sensitive display surface of the tablet computing device. Based upon the route 1066, the tablet computing device 1062 may compute a target distance 1068 and an elevation change 1070 for the task. The GUI 1064 also includes a mode of travel selector 1106 for the user to input the mode of travel (e.g., marching).

The GUI 1064 further includes a load selector 1072, a footwear selector 1074, and a terrain selector 1076. The load selector 1072 indicates a load (e.g., 35 pounds) carried by each of the soldiers 1004 during the march. The footwear selector 1074 indicates a type of footwear (e.g., boots) used during the march, and the terrain selector 1076 indicates a type of terrain traversed during the march (e.g., rocky terrain). The user-input data provided via the GUI 1064 is translated into one or more values that are used to populate the operational task feature vector 264.

In other examples, one or more parameters of the operational task feature vector 264 can be populated based upon the sensor data 212, similar to the training task input feature vector 234. For example, the GUI 1064 of FIG. 8A displays current weather conditions 1078, which can be obtained from the sensor data and used to populate the feature vector.

Referring again to FIG. 4B, at 428, the operational task may be performed by the user at a future time. The method 400 further comprises predicting the one or more target environmental conditions 252 at the future time. For example, referring again to FIG. 8A, the soldiers 1004 may plan to occupy the hilltop 1006 the following day. Accordingly, the GUI 1064 displays a weather forecast 1080 for the day of the operation. The weather forecast 1080 may be used to populate the operational task feature vector 264 of FIG. 5B. One or more other features may also be populated based upon the predicted environmental conditions. For example, it may be inferred that the terrain may be muddy based upon the weather forecast. It will be appreciated that the prediction of the environmental conditions at step 428 is typically not performed by the AI performance model 220, but rather is performed by a separate model such as a weather prediction model, which takes as input a different set of weather-related inputs.

As indicated at 430 of FIG. 4B, the method 400 includes, based on the operational input data 226, using the AI performance model 220 to infer a predicted time elapsed for performance of the operational task. At 434, the method 400 includes outputting a predicted result 222 such as the predicted time elapsed 222A for performance of the operational task. For example, and with reference again to FIG. 5B, the trained performance model 220 is configured to output the predicted time elapsed 222A to perform the operational task. The predicted time elapsed 222A for performance of the operational task may be output to any suitable device or devices. For example, the predicted time elapsed 222A to perform the operational task may be output for display to military leaders, emergency response coordinators, and others who may not be able to directly observe a field environment. In other examples, the predicted time elapsed 222A for performance of the operational task may be output to a server computing device. In yet other examples, the predicted time elapsed for performance of the operational task may be output to one or more user devices (e.g., the tablet computing device 1062 of FIG. 8A).

In some examples, at 432 of FIG. 4B, the method 400 may include receiving operational biometric data such as heart rate 242C, GSR 242D, pulse oximetry data 242E, body temperature 242G, exhaled gas data 242I, heart signal 242J, brain activity 242K (e.g., as measured by electroencephalography, functional magnetic resonance imaging, computed tomography, magnetoencephalography, positron emission tomography, or near infrared spectroscopy), medical test 242L, or other biometric data, and inferring the predicted time elapsed 222A for performance of the operational task may be based at least in part upon the operational biometric data. In the example of FIG. 8A, the tablet computing device 1062 is displaying a dialog box 1082 including a predicted time elapsed 1084A (e.g., 220 minutes) to perform the operational task. The predicted time elapsed 1084A to perform the operational task is based at least in part upon received operational biometric data for at least one of the soldiers 1004 in the environment 1000 of FIG. 1A. The GUI 1064 may additionally or alternatively display a readiness confidence score 1084B associated with the predicted elapsed time 1084A.

For example, the GUI 1064 may display a location of the team 1002 on a contour map 1086 of the environment 1000 of FIG. 1A. The GUI 1064 may also include an indicator box 1088, including indicators 1004A-D for each of the soldiers 1004 in the team 1002. The dialog box 1082 can also display biometric data for the soldier indicated at 1004A, such as the soldier's body temperature 1090 (e.g., 104° F.). The dialog box 1082 may also include text 1092 indicating that this soldier is a likely casualty (e.g., due to the soldier's high body temperature). As another example, referring to FIG. 7, one or more pressure sensors 1094A, 1094B located in the soldier's boots 1096A, 1096B may indicate that a user's gait is abnormal, which could indicate an injury. In some examples, the visual indicator 1004A for the soldier may be visually altered to indicate that the soldier is injured. For example, the visual indicator 1004A may change color or flash. The team 1002 may additionally or alternatively appear visually altered on the tablet computing device 1062 to indicate that one or more of its soldiers are injured.

At 436 of FIG. 4B, the method 400 may include receiving a threshold time elapsed for performance of the operational task. The threshold time elapsed for performance of the operational task in the example of FIG. 8A is 90 minutes, as indicated at 1098. In some examples, the threshold time elapsed for performance of the operational task may be received from the user interface device 232. For example, the threshold time 1098 of FIG. 8A may be user input at the tablet computing device 1062. In other examples, the threshold time elapsed for performance of the operational task may be received from one or more remote computing devices. For example, the threshold time elapsed for performance of the operational task may be received from a computing device operated by someone outside of the operational environment 1000 of FIG. 1A. In yet other examples, the threshold time elapsed for performance of the operational task may be output from one or more additional artificial intelligence (AI) models.

At 438 of FIG. 4B, the method 400 may include comparing the predicted time elapsed for performance of the operational task to the threshold time elapsed. In this manner, the performance model may be used to filter assets, such as the soldiers 1004, and identify those that can perform the operational task within a threshold time.

For example, the performance model 220 may indicate that the soldier indicated at 1004A may take 220 minutes to march to the hilltop 1006, which is longer than the threshold time 1098 (e.g., 90 minutes). In some examples, the visual indicator 1004A for the soldier may be visually altered (e.g., to change color or flash) to indicate that it is not likely that the soldier will perform the operational task within the threshold time. The team 1002 may additionally or alternatively appear visually altered to indicate that one or more of its soldiers are not likely to perform the operational task within the threshold time. In this manner, the GUI 1064 may visually report a status of each asset (e.g., the soldiers and the team) vis a vis a mission goal. The visual indicators may also be updated in response to changing conditions (e.g., forecast weather conditions, movements, and terrain conditions).

Based on comparing the predicted time elapsed to the threshold time elapsed, the method 400 may include accepting or declining the operational task, as indicated at 440 of FIG. 4B. For example, and with reference now to FIG. 8B, the dialog box 1082 may additionally or alternatively include a recommended action. For example, the dialog box 1082 may include indication text 1100A instructing a user to cancel the operational task. As another example, the dialog box 1082 may include indication text 1100B instructing the user to assign other individuals to the task. As another example, the dialog box 1082 may include indication text 1100C instructing the user to adjust the threshold time, for example to give the team 1002 more time to complete the operational task. As another example, the dialog box 1082 may include indication text 1100D instructing the user to split up the team 1002. For example, by running iterated simulations of different environmental conditions, the AI performance model may indicate that the soldier indicated at 1004D can carry more weight, and that by transferring a load carried by the soldier indicated at 1004A to the soldier 1004D, the team 1002 may be able to meet the threshold time.

As another example, a computing device (e.g., the user interface device 232, the edge computing device 202, or a remote computing device, such as a server) may automatically designate appropriate individuals who are likely to accomplish the task within the threshold time. In this manner, the performance model may be used to automate task management.

Referring again to FIG. 5B, in some examples, a feedback module 258 is provided to conduct feedback training on the performance model 220. After the predicted time elapsed 222A for performance of the operational task is output, user feedback 260 may be received via a user feedback interface 262. The user feedback interface 262 can be implemented at the user interface device 232 of FIG. 2 or at any other suitable device. In this manner, the user can provide feedback indicating that the predicted time elapsed 222A for performance of the operational task inferred by the performance model 220 was accurate or inaccurate. The feedback 260 is then paired with the operational task 228 as a feedback training data set and used to conduct feedback training on the performance model 220.

In some examples, the tablet computing device 1062 may also be configured to receive feedback for the predicted time elapsed for performance of the operational task. For example, the dialog box 1082 may include a "YES" selector button 1102 that the user may select to indicate that the prediction was accurate. The dialog box 1082 may also include a "NO" selector button 1104. In this manner, the user may provide feedback for the predicted time elapsed for performance of the operational task. The user input feedback is then paired with the operational task feature vector as a feedback training data pair and used to conduct feedback training on the performance model.

In the above-described method 400, the performance model is trained to output predicted time elapsed for performance of the operational task. It will also be appreciated that the performance model may be trained to output any other suitable parameter as described herein. For example, as described in more detail below with reference to FIG. 9, a performance model may be trained using a biometric parameter as ground truth output. In this manner, the performance model may infer a value of the biometric parameter during or after performing the operational task.

With reference now to FIG. 9, a flowchart is illustrated depicting an example method 2000 for determining a user's readiness for an operational task. The following description of method 2000 is provided with reference to the software and hardware components described above and shown in FIGS. 1-8 and 10-11. It will be appreciated that method 2000 also may be performed in other contexts using other suitable hardware and software components.

It will be appreciated that the following description of method 2000 is provided by way of example and is not meant to be limiting. It will be understood that various steps of method 2000 can be omitted or performed in a different order than described, and that the method 2000 can include additional and/or alternative steps relative to those illustrated in FIG. 9 without departing from the scope of this disclosure.

The method 2000 includes a training phase 2002 and a run-time phase 2004. During the training phase 2002, for each of a plurality of user training sessions associated with a training task performed by a user, the method 2000 comprises, at 2006, receiving training input data. The training input data includes, for each user training session, a training data pair including, as input, a distance of travel, a mode of travel, one or more environmental conditions in which the training task is performed during the training session, and a time elapsed for performance of the training task by the user during the training session, and a health condition as ground truth output, the one or more environmental conditions being selected from a plurality of predefined environmental conditions.

The health condition may include any suitable conditions. Heat stroke is one example of a health condition that can be diagnosed by a medical professional, and the diagnosis may be used as the ground truth output during the training session. In other examples, as indicated at 2007, the health condition may include a biometric parameter measured by a biometric sensor. As indicated at 2008, the biometric parameter may be selected from the group consisting of heart rate data, heart signal data, pulse oximetry data, caloric data, body temperature data, galvanic skin response data, exhaled gas composition data, and medical test data. Next, at 2010, the method 2000 includes training an AI performance model that models user performance of the training task based on the training data pairs.

In the run-time phase 2004, the method 2000 includes, at 2012, receiving operational input data associated with an operational task performed by the user, the operational input data including a target distance of travel, a target mode of travel, one or more target environmental conditions in which the operational task is performed, and a time elapsed for performance of the operational task. At 2014, the method 2000 includes based on the operational input data, using the AI performance model to infer a predicted health condition value. At 2016, the method 2000 includes outputting the predicted health condition value. Where the health condition includes the biometric parameter measured by the biometric sensor, the predicted health condition includes a predicted biometric parameter value.

In some embodiments, the methods and processes described herein may be tied to a computing system of one or more computing devices. In particular, such methods and processes may be implemented as a computer-application program or service, an application-programming interface (API), a library, and/or other computer-program product.

FIG. 10 depicts one example of a user computing device in the form of a tablet computing device 1101 that can be used to infer a predicted biometric parameter value. The tablet computing device 1101 displays a GUI 1103 for the four-mile march to the hilltop 1006 of FIG. 1A. The GUI 1103 includes user-operable selection features configured to receive user-input data as described above with reference to FIGS. 8A-8B. The user input data may include the distance, mode of travel, travel time, and an indication of the conditions under which the operational task is accomplished. The tablet computing device 1101 is also configured to display a dialog box 1105 indicating a predicted biometric parameter in the form of a predicted body temperature 1107 (e.g., 104° F.) for the soldier 1004A of FIG. 1A after the travel time has elapsed.

Figure 11:
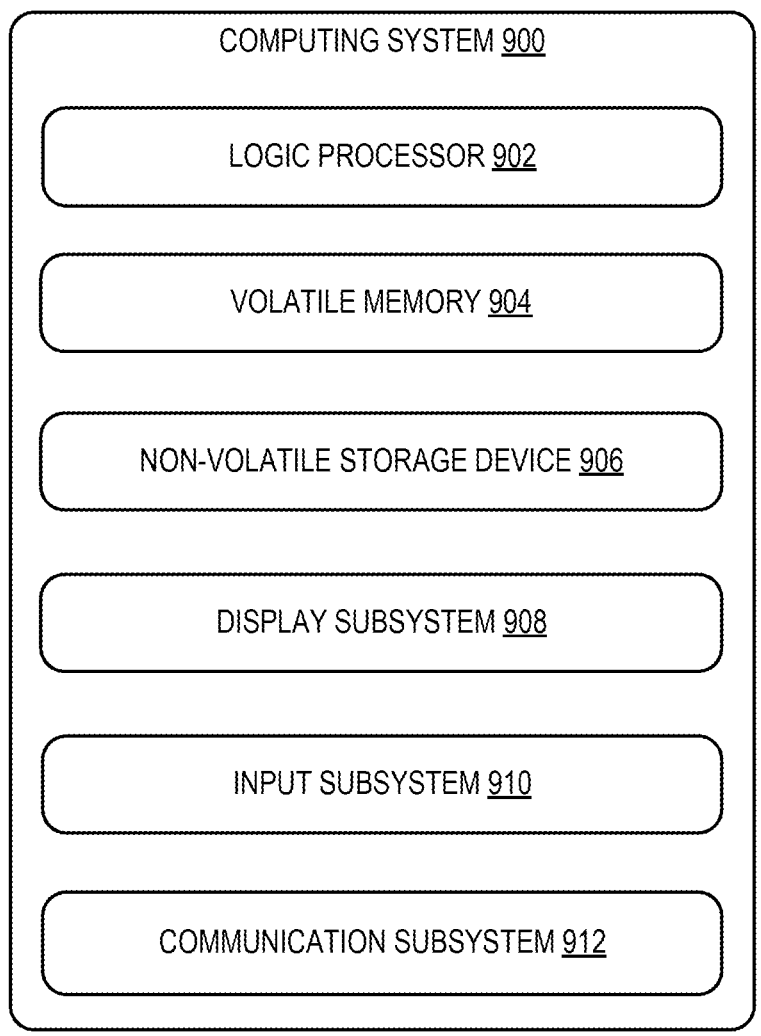
FIG. 11 shows a schematic diagram of an example computing system, according to one example embodiment.

FIG. 11 schematically shows an example of a computing system 900 that can enact one or more of the devices and methods described above. Computing system 900 is shown in simplified form. Computing system 900 may take the form of one or more personal computers, server computers, tablet computers, home-entertainment computers, network computing devices, gaming devices, mobile computing devices, mobile communication devices (e.g., smart phone), and/or other computing devices, and wearable computing devices such as smart wristwatches and head mounted augmented reality devices. In some examples, the computing system 900 may embody the user interface device 232 of FIG. 2, the edge computing device 202 of FIG. 2, the computing device 300 of FIG. 3, the tablet computing device 1020 of FIGS. 6A-6B, or the tablet computing device 1062 of FIGS. 8A-8B.

The computing system 900 includes a logic processor 902, volatile memory 904, and a non-volatile storage device 906. The computing system 900 may optionally include a display subsystem 908, input subsystem 910, communication subsystem 912, and/or other components not shown in FIG. 11.

Logic processor 902 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 902 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor may be virtualized and executed by remotely accessible, networked computing devices configured in a cloud-computing configuration. In such a case, these virtualized aspects are run on different physical logic processors of various different machines, it will be understood.

Non-volatile storage device 906 includes one or more physical devices configured to hold instructions executable by the logic processors to implement the methods and processes described herein. When such methods and processes are implemented, the state of non-volatile storage device 906 may be transformed—e.g., to hold different data.

Non-volatile storage device 906 may include physical devices that are removable and/or built in. Non-volatile storage device 906 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 906 may include nonvolatile, dynamic, static, read/write, read-only, sequential-access, location-addressable, file-addressable, and/or content-addressable devices. It will be appreciated that non-volatile storage device 906 is configured to hold instructions even when power is cut to the non-volatile storage device 906.

Volatile memory 904 may include physical devices that include random access memory. Volatile memory 904 is typically utilized by logic processor 902 to temporarily store information during processing of software instructions. It will be appreciated that volatile memory 904 typically does not continue to store instructions when power is cut to the volatile memory 904.

Aspects of logic processor 902, volatile memory 904, and non-volatile storage device 906 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module" and "program" may be used to describe an aspect of computing system 900 typically implemented in software by a processor to perform a particular function using portions of volatile memory, which function involves transformative processing that specially configures the processor to perform the function. Thus, a module or program may be instantiated via logic processor 902 executing instructions held by non-volatile storage device 906, using portions of volatile memory 904. It will be understood that different modules and/or programs may be instantiated from the same application, service, code block, object, library, routine, API, function, etc. Likewise, the same module and/or program may be instantiated by different applications, services, code blocks, objects, routines, APIs, functions, etc. The terms "module" and "program" may encompass individual or groups of executable files, data files, libraries, drivers, scripts, database records, etc.

When included, display subsystem 908 may be used to present a visual representation of data held by non-volatile storage device 906. The visual representation may take the form of a GUI. As the herein described methods and processes change the data held by the non-volatile storage device, and thus transform the state of the non-volatile storage device, the state of display subsystem 908 may likewise be transformed to visually represent changes in the underlying data. Display subsystem 908 may include one or more display devices utilizing virtually any type of technology. Such display devices may be combined with logic processor 902, volatile memory 904, and/or non-volatile storage device 906 in a shared enclosure, or such display devices may be peripheral display devices.

When included, input subsystem 910 may comprise or interface with one or more user-input devices such as a keyboard, mouse, touch screen, or game controller. In some examples, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 912 may be configured to communicatively couple various computing devices described herein with each other, and with other devices. Communication subsystem 912 may include wired and/or wireless communication devices compatible with one or more different communication protocols. For example, the communication subsystem may be configured for communication via a wireless telephone network, or a wired or wireless local- or wide-area network. In some examples, the communication subsystem may allow computing system 900 to send and/or receive messages to and/or from other devices via a network such as the Internet.

The following paragraphs further describe the systems and methods of the present disclosure. According to a first aspect, the present disclosure includes a method for determining a user's readiness for an operational task, the method comprising: at one or more processors of one or more computing devices: during a training phase, for each of a plurality of user training sessions associated with a training task performed by a user: receiving training input data including, for each user training session, a training data pair including, as input, a distance of travel, a mode of travel, and one or more environmental conditions in which the training task is performed during the training session, and as ground truth output, a time elapsed for performance of the training task by the user during the training session, the one or more environmental conditions being selected from a plurality of predefined environmental conditions; training an artificial intelligence (AI) performance model that models user performance of the training task based on the training data pairs; and during a run-time phase: receiving operational input data associated with an operational task performed by the user, the operational input data including a target distance of travel, a target mode of travel, and one or more target environmental conditions in which the operational task is performed; based on the operational input data, using the AI performance model to infer a predicted time elapsed for performance of the operational task; and outputting the predicted time elapsed for performance of the operational task.

According to this aspect, the method can further comprise: providing a sensor to receive sensor data, the sensor data indicating the time elapsed for performance of the training task during the training phase. It will be appreciated that receiving the sensor data can comprise receiving one or more of location data or motion data of the user, and receiving the sensor data can comprise receiving the motion data from one or more wearable kinematic sensors worn by the user. The sensor data can include one or more of terrain-related data or weather data, and the method can further comprise analyzing the sensor data to determine the one or more environmental conditions in which the training task is performed. Further, receiving the sensor data can comprise receiving biometric data for the user. Further, receiving the biometric data can comprise receiving one or more of heart rate data, pulse oximetry data, caloric data, body temperature data, pressure data, shock data, galvanic skin response data, exhaled gas composition data, heart signal data, brain activity data, or medical test data. This aspect of the method can further comprise receiving operational biometric data, wherein inferring the predicted time elapsed for performance of the operational task is based at least in part upon the operational biometric data. Receiving the biometric data can comprise receiving one or more of heart rate data, pulse oximetry data, caloric data, body temperature data, pressure data, shock data, galvanic skin response data, exhaled gas composition data, heart signal data, brain activity data, or medical test data. The method can further comprise: receiving operational biometric data; and wherein inferring the predicted time elapsed for performance of the operational task is based at least in part upon the operational biometric data.

According to this aspect, method further comprises: providing a training interface to receive a user input including one or more of the distance of travel, the mode of travel, or the one or more environmental conditions in which the training task is performed.

According to this aspect, the one or more environmental conditions can include one or more of weather conditions or terrain conditions.

According to this aspect, the operational task can be performed by the user at a future time, and the method can further comprise predicting the one or more target environmental conditions at the future time.

According to this aspect, the method can further comprise: receiving a threshold time elapsed for performance of the operational task; comparing the predicted time elapsed for performance of the operational task to the threshold time elapsed; and based on comparing the predicted time elapsed to the threshold time elapsed, accepting or declining the operational task.

According to another aspect, an edge computing device is disclosed, comprising: a processor; and a memory storing instructions executable by the processor to: during a training phase, for each of a plurality of user training sessions associated with a training task performed by a user: receive training input data including, for each user training session, a training data pair including, as input, a distance of travel, a mode of travel, and one or more environmental conditions in which the training task is performed during the training session, and as ground truth output, a time elapsed for performance of the training task by the user during the training session, the one or more environmental conditions being selected from a plurality of predefined environmental conditions; train an artificial intelligence (AI) performance model that models user performance of the training task based on the training data pairs; and, during a run-time phase: receive operational input data associated with an operational task performed by the user, the operational input data including a target distance of travel, a target mode of travel, and one or more environmental conditions in which the operational task is performed; based on the operational input data, use the AI performance model to infer a predicted time elapsed for performance of the operational task, and output the predicted time elapsed for performance of the operational task.

In this aspect, the instructions can be further executable to receive sensor data, the sensor data indicating the time elapsed for performance of the training task during the training phase. The instructions can be further executable to receive, via a training interface, a user input including one or more of the distance of travel, the mode of travel, or the one or more environmental conditions in which the training task is performed. The sensor data can comprise one or more of location data or motion data of the user. The one or more environmental conditions can include one or more of weather conditions or terrain conditions. Receiving the sensor data can comprises receiving biometric data for the user.

In this aspect, the instructions can be further executable to: receive a threshold time elapsed for performance of the operational task; compare the predicted time elapsed for performance of the operational task to the threshold time elapsed; and based on comparing the predicted time elapsed to the threshold time elapsed, accept or decline the operational task.

According to another aspect, a system for determining a user's readiness for an operational task is provided, the system comprising: one or more sensors configured to output sensor data indicating a time elapsed for performance of a training task during a training phase; an edge computing device, comprising, a processor, and memory storing instructions executable by the processor to, during the training phase, for each of a plurality of user training sessions associated with the training task: receive the sensor data from the one or more sensors; receive training input data including, for each user training session, a training data pair including, as input, a distance of travel, a mode of travel, and one or more environmental conditions in which the training task is performed during the training session, and as ground truth output, the time elapsed for performance of the training task by the user during the training session, the one or more environmental conditions being selected from a plurality of predefined environmental conditions, wherein the time elapsed for performance of the training task is based upon the sensor data received from the one or more sensors; train an artificial intelligence (AI) performance model that models user performance of the training task based on the training data pairs, and, during a run-time phase: receive operational input data associated with an operational task performed by the user, the operational input data including a target distance of travel, a target mode of travel, and one or more target environmental conditions in which the operational task is performed, based on the operational input data, use the AI performance model to infer a predicted time elapsed for performance of the operational task, and output the predicted time elapsed for performance of the operational task.

According to another aspect, a method for determining a user's readiness for an operational task is provided, the method comprising: at one or more processors of one or more computing devices: during a training phase, for each of a plurality of user training sessions associated with a training task performed by a user: receiving training input data including, for each user training session, a training data pair including, as input, a distance of travel, a mode of travel, one or more environmental conditions in which the training task is performed during the training session, and a time elapsed for performance of the training task by the user during the training session, and a health condition as ground truth output, the one or more environmental conditions being selected from a plurality of predefined environmental conditions; training an artificial intelligence (AI) performance model that models user performance of the training task based on the training data pairs; and, during a run-time phase: receiving operational input data associated with an operational task performed by the user, the operational input data including a target distance of travel, a target mode of travel, one or more target environmental conditions in which the operational task is performed, and a time elapsed for performance of the operational task; based on the operational input data, using the AI performance model to infer a predicted health condition value; and outputting the predicted health condition value. The health condition can include a biometric parameter measured by a biometric sensor, and the predicted health condition can include a predicted biometric parameter value. The biometric parameter can be selected from the group consisting of heart rate data, heart signal data, pulse oximetry data, caloric data, body temperature data, galvanic skin response data, exhaled gas composition data, and medical test data.

It will be understood that the configurations and/or approaches described herein are exemplary in nature, and that these specific embodiments or examples are not to be considered in a limiting sense, because numerous variations are possible. The specific routines or methods described herein may represent one or more of any number of strategies. As such, various acts illustrated and/or described may be performed in the sequence illustrated and/or described, in other sequences, in parallel, or omitted. Likewise, the order of the above-described methods may be changed.

The subject matter of the present disclosure includes all novel and non-obvious combinations and sub-combinations of the various methods, systems and configurations, and other features, functions, acts, and/or properties disclosed herein, as well as any and all equivalents thereof.

The invention claimed is:

1. A method for determining a user's readiness for an operational task, the method comprising:
   at one or more processors of a wearable edge computing device co-located with the user:
   during a training phase, for each of a plurality of user training sessions associated with a training task performed by a user, wherein the training task comprises foot travel during the user training session:
      receiving location sensor data from a location sensor communicatively coupled to the one or more processors of the wearable edge computing device, wherein the location sensor comprises one or more of an accelerometer or a global positioning system (GPS) sensor;
      using the location sensor data to determine distance of travel and a time elapsed for performance of the training task by the user during the user training session;
      receiving a terrain type and a weather condition in which the training task is performed during the user training session, the terrain type being selected from a plurality of predefined terrain types;
   receiving biometric data for the user from a biometric sensor, the biometric data comprising a biometric parameter, wherein the biometric sensor comprises one or more of a heart rate monitor, a galvanic skin response (GSR) sensor, a pulse oximeter, or a breath gas analyzer;
   generating a training data pair for the user training session, the training data pair including,
      as input, the distance of travel, the weather condition, the terrain type, and the biometric parameter, and
      as ground truth output, the time elapsed determined using the location sensor data;
   training an artificial intelligence (AI) performance model that models user performance of the foot travel during the user training session based on the training data pairs for the plurality of the user training sessions; and
during a run-time phase:
   receiving operational input data associated with an operational task performed by the user, the operational task comprising foot travel, the operational input data including a target distance of travel, a target weather condition, a target terrain type in which the operational task is performed, and a value for the biometric parameter for the user during the run-time phase;
   based on the operational input data, using the AI performance model to infer a predicted time elapsed for performance of the operational task;
   outputting the predicted time elapsed for performance of the operational task;
   receiving feedback for the predicted time elapsed for performance of the operational task;
   pairing the feedback with the operational input data as a feedback training data pair; and
   using the feedback training pair to conduct feedback training on the AI performance model.

2. The method of claim 1, further comprising:
   providing a training interface to receive a user input including one or more of the terrain type and the weather condition in which the training task is performed.

3. The method of claim 1, wherein receiving the location sensor data comprises receiving motion data of the user.

4. The method of claim 3, wherein receiving the location sensor data further comprises receiving the motion data from one or more wearable kinematic sensors worn by the user.

5. The method of claim 1, further comprising receiving one or more of terrain-related sensor data or weather sensor data, the method further comprising analyzing the terrain-related sensor data and/or the weather sensor data to determine the terrain type and/or the weather condition in which the training task is performed.

6. The method of claim 1, wherein receiving the biometric data comprises receiving one or more of heart rate data, pulse oximetry data, galvanic skin response data, or exhaled gas composition data.

7. The method of claim 1, wherein the operational task is to be performed by the user at a future time, the method further comprising predicting one or more of the target weather condition or the target terrain type at the future time.

8. The method of claim 1, further comprising:
   receiving a threshold time elapsed for performance of the operational task;
   comparing the predicted time elapsed for performance of the operational task to the threshold time elapsed; and
   based on comparing the predicted time elapsed to the threshold time elapsed, accepting or declining the operational task.

9. An edge computing device, comprising:
   a processor; and
   a memory storing instructions executable by the processor to:
      during a training phase, for each of a plurality of user training sessions associated with a training task performed by a user, wherein the training task comprises foot travel during the user training session:
         receive location sensor data from a location sensor communicatively coupled to the processor of the edge computing device, wherein the location sensor comprises one or more of an accelerometer or a global positioning system (GPS) sensor;
         use the location sensor data to determine distance of travel and a time elapsed for performance of the training task by the user during the user training session;
         receive a terrain type and a weather condition in which the training task is performed during the user training session, the terrain type being selected from a plurality of predefined terrain types;
receive biometric data for the user from a biometric sensor, the biometric data comprising a biometric parameter, wherein the biometric sensor comprises one or more of a heart rate monitor, a galvanic skin response (GSR) sensor, a pulse oximeter, or a breath gas analyzer;
generate a training data pair for the user training session, the training data pair including,
as input, the distance of travel, the weather condition, the terrain type, and the biometric parameter, and
as ground truth output, the time elapsed determined using the location sensor data;
train an artificial intelligence (AI) performance model that models user performance of the foot travel during the user training session based on the training data pairs for the plurality of the user training sessions; and
during a run-time phase:
receive operational input data associated with an operational task performed by the user, the operational task comprising foot travel, the operational input data including a target distance of travel, a target weather condition, a target terrain type in which the operational task is performed, and a value for the biometric parameter for the user during the run-time phase;
based on the operational input data, use the AI performance model to infer a predicted time elapsed for performance of the operational task;
output the predicted time elapsed for performance of the operational task;
receive feedback for the predicted time elapsed for performance of the operational task;
pair the feedback with the operational input data as a feedback training data pair; and
use the feedback training pair to conduct feedback training on the AI performance model.

10. The edge computing device of claim 9, wherein the instructions are further executable to receive, via a training interface, a user input including one or more of the terrain type and the weather condition in which the training task is performed.

11. The edge computing device of claim 9, wherein the location sensor data comprises motion data of the user.

12. The edge computing device of claim 9, wherein the instructions are further executable to:
receive a threshold time elapsed for performance of the operational task;
compare the predicted time elapsed for performance of the operational task to the threshold time elapsed; and
based on comparing the predicted time elapsed to the threshold time elapsed, accept or decline the operational task.

13. A system for determining a user's readiness for an operational task, the system comprising:
one or more location sensors configured to output location sensor data indicating a time elapsed for performance of a training task during a training phase, wherein the one or more location sensors comprise one or more of an accelerometer or a global positioning system (GPS) sensor;
one or more biometric sensors, wherein the one or more biometric sensors comprise one or more of a heart rate monitor, a galvanic skin response (GSR) sensor, a pulse oximeter, or a breath gas analyzer;
an edge computing device, comprising,
a processor communicatively coupled to the one or more location sensors, and
a memory storing instructions executable by the processor to,
during the training phase, for each of a plurality of user training sessions associated with the training task, wherein the training task comprises foot travel during the user training session:
receive the location sensor data from the one or more location sensors;
use the location sensor data to determine distance of travel and a time elapsed for performance of the training task by the user during the user training session;
receive a terrain type and a weather condition in which the training task is performed during the user training session, the terrain type being selected from a plurality of predefined terrain types;
receive biometric data for the user from the one or more biometric sensors, the biometric data comprising at least one biometric parameter;
generate a training data pair for the user training session, the training data pair including,
as input, the distance of travel, the weather condition, the terrain type and the at least one biometric parameter, and
as ground truth output, the time elapsed determined using the location sensor data;
train an artificial intelligence (AI) performance model that models user performance of the foot travel during the user training session based on the training data pairs for the plurality of the user training sessions, and
during a run-time phase:
receive operational input data associated with an operational task performed by the user, the operational task comprising foot travel, the operational input data including a target distance of travel, a target weather condition, a target terrain type in which the operational task is performed, and a value for the biometric parameter for the user during the run-time phase,
based on the operational input data, use the AI performance model to infer a predicted time elapsed for performance of the operational task,
output the predicted time elapsed for performance of the operational task;
receive feedback for the predicted time elapsed for performance of the operational task;
pair the feedback with the operational input data as a feedback training data pair; and
use the feedback training pair to conduct feedback training on the AI performance model.

14. A method for determining a user's readiness for an operational task, the method comprising:
at one or more processors of a wearable edge computing device co-located with the user:
during a training phase, for each of a plurality of user training sessions associated with a training task performed by the user, wherein the training task comprises foot travel during the user training session:

receiving location sensor data from a location sensor communicatively coupled to the one or more processors of the wearable edge computing device, wherein the location sensor comprises one or more of an accelerometer or a global positioning system (GPS) sensor;

using the location sensor data to determine distance of travel and a time elapsed for performance of the training task by the user during the user training session;

receiving a terrain type and a weather condition in which the training task is performed during the user training session, the terrain type being selected from a plurality of predefined terrain types;

receiving biometric data for the user from a biometric sensor, the biometric data comprising a biometric parameter, wherein the biometric sensor comprises one or more of a heart rate monitor, a galvanic skin response (GSR) sensor, a pulse oximeter, or a breath gas analyzer;

generating a training data pair for the user training session, the training data pair including,
as input, the distance of travel, the weather condition, the terrain type, and the time elapsed for performance of the training task by the user during the training session determined using the location sensor data, and
as ground-truth output, the biometric parameter;

training an artificial intelligence (AI) performance model that models user performance of the foot travel during the user training session based on the training data pairs for the plurality of the user training sessions; and during a run-time phase:
receiving operational input data associated with an operational task performed by the user, the operational task comprising foot travel, the operational input data including a target distance of travel, a target weather condition, a target terrain type in which the operational task is performed, and a time elapsed for performance of the operational task;
based on the operational input data, using the AI performance model to infer a predicted value for the biometric parameter for the user during the run-time phase;
outputting the predicted value for the biometric parameter;
receiving feedback for the predicted value for the biometric parameter;
pairing the feedback with the operational input data as a feedback training data pair; and
using the feedback training pair to conduct feedback training on the AI performance model.

15. The method of claim 14, wherein the biometric parameter is selected from the group consisting of heart rate data, pulse oximetry data, galvanic skin response data, and exhaled gas composition data.

16. The method of claim 1, wherein the weather condition is selected from the group consisting of temperature, wind, humidity, precipitation, and UV index; and
wherein the terrain type is selected from the group consisting of pavement, soft earth, hard earth, gravel, rocky terrain, brush, marsh, and sand.

17. The edge computing device of claim 9, wherein the weather condition is selected from the group consisting of temperature, wind, humidity, precipitation, and UV index; and
wherein the terrain type is selected from the group consisting of pavement, soft earth, hard earth, gravel, rocky terrain, brush, marsh, and sand.

18. The method of claim 1, wherein receiving the biometric data further comprises receiving one or more of caloric data, body temperature data, pressure data, shock data, heart signal data, brain activity data, or medical test data.

19. The system of claim 13, wherein the weather condition is selected from the group consisting of temperature, wind, humidity, precipitation, and UV index; and
wherein the terrain type is selected from the group consisting of pavement, soft earth, hard earth, gravel, rocky terrain, brush, marsh, and sand.

20. The system of claim 13, wherein the operational task is to be performed by the user at a future time, and wherein the instructions are further executable to, predict one or more of the target weather condition or the target terrain type at the future time.

21. The method of claim 14, wherein the operational task is to be performed by the user at a future time, the method further comprising predicting one or more of the target weather condition or the target terrain type at the future time.

22. The system of claim 13, wherein the instructions are further executable to:
receive a threshold time elapsed for performance of the operational task;
compare the predicted time elapsed for performance of the operational task to the threshold time elapsed; and
based on comparing the predicted time elapsed to the threshold time elapsed, accept or decline the operational task.

23. The method of claim 14, further comprising receiving one or more of terrain-related sensor data or weather sensor data, the method further comprising analyzing the terrain-related sensor data and/or the weather sensor data to determine the terrain type and/or the weather condition in which the training task is performed.

* * * * *